(12) United States Patent
Otvos et al.

(10) Patent No.: US 9,073,965 B2
(45) Date of Patent: Jul. 7, 2015

(54) ADIPONECTIN RECEPTOR AGONISTS AND METHODS OF USE

(75) Inventors: Laszlo Otvos, Audubon, PA (US); Eva Surmacz, Philadelphia, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 57 days.

(21) Appl. No.: 14/110,813

(22) PCT Filed: Apr. 11, 2012

(86) PCT No.: PCT/US2012/033099
§ 371 (c)(1),
(2), (4) Date: Oct. 9, 2013

(87) PCT Pub. No.: WO2012/142142
PCT Pub. Date: Oct. 18, 2012

(65) Prior Publication Data
US 2014/0057833 A1     Feb. 27, 2014

Related U.S. Application Data

(60) Provisional application No. 61/474,539, filed on Apr. 12, 2011.

(51) Int. Cl.
*A61K 38/04* (2006.01)
*C07K 7/00* (2006.01)
*C07K 7/06* (2006.01)
*C07K 14/575* (2006.01)
*C07K 14/47* (2006.01)
*A61K 38/00* (2006.01)

(52) U.S. Cl.
CPC . *C07K 7/06* (2013.01); *A61K 38/00* (2013.01); *C07K 14/5759* (2013.01); *C07K 14/4702* (2013.01)

(58) Field of Classification Search
None
See application file for complete search history.

(56) References Cited

U.S. PATENT DOCUMENTS

| | | | |
|---|---|---|---|
| 7,430,476 B2 | 9/2008 | Carr et al. | 702/19 |
| 7,709,607 B2 | 5/2010 | Zalevsky et al. | 530/350 |
| 2003/0224425 A1 | 12/2003 | Blondel et al. | 435/6 |
| 2006/0052292 A1 | 3/2006 | Rasmussen et al. | 514/12 |
| 2007/0015909 A1* | 1/2007 | Cash et al. | 530/350 |
| 2008/0221305 A1 | 9/2008 | Chen et al. | 530/350 |
| 2010/0016216 A1 | 1/2010 | Cooper et al. | 514/8 |
| 2010/0189682 A1 | 7/2010 | Schellenberger et al. | 424/85.2 |

FOREIGN PATENT DOCUMENTS

WO    WO-2006074432    * 7/2006

OTHER PUBLICATIONS

Grossmann, et al., "Effects of adiponectin on breast cancer cell growth and signaling", *British Journal of Cancer* (2008) 98, 370-379.
Korner, et al., "Total and High-Molecular-Weight Adiponectin in Breast Cancer: In Vitro and In Vivo Studies", *The Journal of Clinical Endocrinology & Metabolism* 92(3): 1041-1048, 2007.
Otvos, et al., "Design and development of a peptide-based adiponectin receptor agonist for cancer treatment", *BMC Biotechnology* 2011, 11: 90.
Williams, et al., "Adiponectin receptor expression is elevated in colorectal carcinomas but not in gastrointestinal stromal tumors", *Endocrine-Related Cancer* (2008) 15 289-299.
Wang, et al., "Adiponectin Receptor 1 Gene (ADIPOR1) as a Candidate for Type 2 Diabetes and Insulin Resistance", *Diabetes*, vol. 53, Aug. 2004, 2132-2136.

* cited by examiner

*Primary Examiner* — Satyanarayana R Gudibande
(74) *Attorney, Agent, or Firm* — Drinker Biddle & Reath LLP

(57) ABSTRACT

Short peptide mimetics of adiponectin suitable for development as pharmaceutical agonists in the treatment of cellular proliferative disorders such as cancer and atherosclerosis are provided.

13 Claims, 5 Drawing Sheets

ADIPONECTIN RECEPTOR AGONISTS AND METHODS OF USE

CROSS-REFERENCE TO RELATED APPLICATIONS

The benefit of the filing date of U.S. Provisional Patent Application No. 61/474,539, filed Apr. 12, 2011, is hereby claimed. The entire disclosure of the aforesaid application is incorporated herein by reference.

REFERENCE TO GOVERNMENT GRANT

This invention was made with government support under W81XWH-09-1-0332 awarded by the Department of Defense and NIH-INBRE 1 P20 RR16469 awarded by the National Institutes of Health. The government has certain rights in the invention.

FIELD OF THE INVENTION

The invention relates to adiponectin peptide fragments and adiponectin peptide fragment derivatives, and their use as agonists of the adiponectin receptor.

BACKGROUND OF THE INVENTION

Cellular proliferative disorders such as cancer are among the most common causes of death in developed countries. For diseases for which treatments exist, such as cancer, despite continuing advances, currently used treatments exhibit undesirable side effects and limited efficacy. Identifying new effective drugs for cellular proliferative disorders, including cancer, is a continuing focus of medical research.

Obesity is an established risk factor for the development of approximately 30 different diseases and disorders, including cardiovascular and inflammation diseases, and cancer. Obesity has been identified as a risk factor for postmenopausal breast cancer and excess fat tissue (especially abdominal) has been associated with worse response to chemotherapy and shorter disease-free survival, regardless of menopausal status. Schaffler, A., Scholmerich, J., Buechler, C. (2007) *Nat Clin Pract Endocrinol Metab* 3:345-54; Vona-Davis, L. Rose, D P. (2007) *Endocr Relat Cancer* 14:189-206. While several adipose tissue-derived factors (e.g. estrogens, fatty acids, insulin-like growth factors, IL-6) have been proposed as possible mediators of the obesity-breast cancer link, recent data emphasize the roles of two adipokines: leptin and adiponectin. Cleary, M P., Ray, A., Rogozina, O P., Dogan, S., Grossmann, M E. (2009) *Front Biosci (School Ed)* 1:329-57. Cleary, M P., Grossman, M E. Ray, A. (2010) *Vet Pathol* 47:202-13. Although the molecular basis of this link is yet to be elucidated, recent studies have suggested that detrimental effects of obesity are mediated by fat tissue-derived adipokines, such as leptin, which is elevated in overweight people.

Adiponectin is a cytokine synthesized in and secreted by adipocytes. Adiponectin is elevated in lean individuals and low in obese people. Adiponectin is known to be a beneficial hormone, with clear catabolic effects on a number of metabolic processes, including glucose regulation and fatty acid metabolism. In addition, adiponectin has been shown to be a potent negative regulator of cancer cell growth and might play a preventive role against cancer development. Adiponectin is found in human serum at concentrations of 2-20 µg/ml. Grossmann, M E., Nkhata, K J., Mizuno, N K., Ray, A., Cleary, M P. (2008) *Br J Cancer* 98:370-9. Circulating adiponectin levels are inversely correlated with body mass index (BMI); in contrast, serum leptin positively correlates with BMI. Ryan, A S., Berman, D M., Nicklas, B J., Sinha, M., Gingerich, R L., Meneilly, G S, et al. (2003) *Diabetes Care* 26:2383-8. Wauters, M., Considine, R V., Van Gaal, L F. (2000) *Eur J Endocrinol* 143:293-311. Adiponectin levels are reduced in conditions of insulin resistance and cardiovascular disease, and even appear to precede these disorders. Yamamoto, Y., Hiroshe, H., Saito, I., Nishikai, K., Saruta, T. (2004) *J Clin Endocrinol Metab* 89:87-90. Furthermore, high circulating adiponectin levels correlate with reduced cancer risk, while low levels of the cytokine are associated with the presence of cancer. Barb, D., Williams C J., Neuwirth, A K., Mantzoros, C S. (2007) *Am J Clin Nutr* 86:s858-66. In general, adiponectin is considered a protective hormone: it exerts anti-diabetic, anti-inflammatory and anti-cancer effects. Adiponectin circulates in trimeric, hexameric, and higher order complexes. Fang, X., Sweeney, G. (2006) *Biochem Soc Trans* 34:798-801. The C-terminal half of the protein representing the globular domain exhibits potent metabolic effects in various tissues. Tomas, E., Tsao, T S., Saha, A K., Murrey, H E., Zhang, C C., Itani, S I., et al. (2002) *Proc Natl Acad Sci USA* 99:16309-13.

Two adiponectin receptors have been identified, AdipoR1 and AdipoR2. Yamauchi, T., Kamon, J., Ito, Y., Tsuchida, A., Yokomizo, T., Kita, S. et al. (2003) *Nature* 423:762-9. AdipoR1 is a high-affinity receptor for globular adiponectin and a low affinity receptor for the full-sized ligand. Wang, H., Zhang, H., Jia, Z. Craig, R. Wang, X., Elbein, S. C. (2004) *Diabetes* 53:2132-6. Both adiponectin receptors are 7-channel integral membrane proteins containing the N-terminal intracellular portion and the C-terminal extracellular portion (an orientation that is exactly the opposite of other G-protein coupled receptors). T-cadherin, a unique cadherin molecule, has been characterized as a third adiponectin receptor on vascular endothelial cells and smooth muscle. However, T-cadherin is just a co-receptor—it does not appear to play a role in direct ligand binding. AdipoR1 has 4 very short extracellular domains, 13, 6, 11 and 16 residues, respectively.

Adiponectin has a stimulatory effect on the phosphorylation and subsequent inactivation of 5'-AMP-activated protein kinase (AMPK), and on acetyl coenzyme A carboxylase (ACC), which is the downstream substrate of AMPK. Yamauchi et al. (2002) *Nature Medicine* 8:1288-95. In addition, adiponectin can stimulate extracellular-signal-regulated kinases 1 and 2 (ERK1/2), and activate peroxisome proliferator-activated receptor-α (PPARα) and stress responsive c-Jun N-terminal kinase (JNK). Yamauchi et al. (2003) *J Biol Chem* 278:2461-8. Adiponectin has also been shown to inhibit gene expression regulated by two essential transcription factors involved in growth and inflammation, respectively: signal transducer and activator of transcription 3 (STAT3) factor and nuclear factor-kB (NF-kB). Barb, D., Williams, C J., Neuwirth, A K., Mantzoros, C S. (2007) *Am J Clin Nutr* 86:s858-66. Miyazaki, T., Bub, J D., Uzuki, M., Iwamoto, Y. (2005) *Biochem Biophys Res Commun* 333:79-87. Targeted disruption experiments suggest that AdipoR1 signals mainly through AMPK, while AdipoR2 through PPARα pathways. Yamauchi, T., Nio, Y., Maki, T., Kobayashi, M., Takazawa, T., Iwabu, M. et al. (2007). *Nat Med* 13:332-9.

Interestingly, adiponectin may exert its biological activity indirectly, through selective sequestration of different growth factors (e.g., basic fibroblast growth factor, platelet-derived growth factor BB, heparin-binding epidermal growth factor) and inhibition of their normal receptor binding. These interactions involve specific oligomeric forms of adiponectin.

Barb, D., Williams, C J., Neuwirth, A K., Mantzoros, C S. (2007) *Am J Clin Nutr* 86:s858-66. Wang et al. (2005) *J Biol Chem* 280:18341-7.

Adiponectin and Breast Cancer.

Adiponectin is thought to counteract the carcinogenic effects of fat-derived factors, including leptin. Cleary M P., Ray, A., Rogozina, O P., Dogan, S., Grossmann, M E. (2009) *Front Biosci (Schol Ed)* 1:329-57. Cleary, M P., Grossmann, M E., Ray, A., (2010) *Vet Pathol* 47:202-13. Jarde, T., Caldefie-chezet, F., Goncalves-Mendes, N., Mishellany, F., Buechler, C., Penault-Llorca, F. et al. (2009) *Endocr Relat Cancer* 16:1197-210. Several epidemiological studies found an inverse relation between adiponectin levels and breast cancer risk. Barb, D., Williams, C J., Neuwirth, A K., Mantzoros, C S. (2007) *Am J Clin Nutr* 86:s858-66. Miyoshi, Y., Funahashi, T., Kihara, S., Taguchi, T., Tamaki, Y., Matsuzawa, Y. et al. (2003) *Clin Cancer Res* 9:5699-704. Mantzoros, C., Petridou, E., Dessypris, N., Chavelas, C., Dalamaga, M., Alexe D M. et al. (2004) J Clin Endocrinol Metab 89:1102-7. Chen, D C., Chung, Y F., Yeh, Y T., Chaung, H C., Kuo, F C., Fu, O Y. et al. (2006) Cancer Lett 237:109-14. In breast cancer patients, adiponectin levels and the adiponectin:leptin ratio are reduced relative to that found in control women. Cleary M P., Ray, A., Rogozina, O P., Dogan, S., Grossmann, M E. (2009) *Front Biosci (Schol Ed)* 1:329-57. Cleary, M P., Grossmann, M E., Ray, A., (2010) *Vet Pathol* 47:202-13. Chen, D C., Chung, Y F., Yeh, Y T., Chaung, H C., Kuo, F C., Fu, O Y. et al. (2006) *Cancer Lett* 237:109-14. Moreover, patients with low adiponectin levels have more aggressive tumors and higher frequency of lymph node metastasis. Schaffler, A., Scholmerich, J., Buechler, C. (2007) *Nat Clin Pract Endocrinol Metab* 3:345-54. Hou, W K., Xu, Y X., Yu, T., Zhang, L., Zhang, W W., Fu, C L. et al. (2007) *Chin Med J (Engl)* 120:1592-6.

In vitro studies have confirmed the anti-neoplastic role of adiponectin. The hormone reduces proliferation in MCF7, MDA-MB-231, and T47D breast cancer cell lines, although some discrepancies regarding the response of individual cell lines were noted by different investigators. Dieudonne, M N., Bussiere, M., Dos Santos, E., Leneveu, M C., Giudicelli, Y., Pecquery, R. (2006) *Biochem Biophys Res Commun* 345:271-9. Kang, J H., Lee, Y Y., Yu, B Y., Yang, B S., Cho, K H., Yoon, D K. et al. (2005) *Arch Pharm Res* 28:1263-9. Korner, A., Pazaitou-Panayiotou, K., Kelesidis, T., Kelesidis, I. Williams, C J., Kaprara, A. et al. (2007) *J Clin Endocrinol Metab* 92:1041-8. In MCF cells, the inhibitory effect is associated with increased activation of AMPK and reduced MAPK signaling. Dieudonne, M N., Bussiere, M., Dos Santos, E., Leneveu, M C., Giudicelli, Y., Pecquery, R. (2006) *Biochem Biophys Res Commun* 345:271-9. In MDA-MB-231 cells, adiponectin blocks the Akt kinase and glycogen synthase kinase/β-catenin pathway. Wang, Y., Lam, J B., Lam, K S., Liu, J. Lam, M C., Hoo, R L. et al. (2006) *Cancer Res* 66:11462-70. Interestingly, adiponectin can also inhibit breast cancer cell migration and invasion. Taliaferro-Smith, L., Nagalingam, A., Zhong, D. Zhu, W. Saxena, N K., Sharma, D. (2009) *Oncogene* 28:2621-33. In animal models, adiponectin suppresses the growth of T47D and MDA-MB-231 xenografts, and in some experiments reduces tumor neoangiogenesis. Cleary, M P., Grossmann, M E., Ray, A., (2010) *Vet Pathol* 47:202-13. Wang, Y., Lam, J B., Lam, K S., Liu, J. Lam, M C., Hoo, R L. et al. (2006) *Cancer Res* 66:11462-70. Saxena, N K., Sharma, D. (2010) Cell Adh Migr 4(3):258-62. AdipoR1 and AdipoR2 have been detected in human breast cancer specimens, but at present, there is no consensus regarding their association with clinicopathological parameters. Pfeiler, G., Treeck, O., Wenzel, G., Goerse, R., Hartmann, A., Schmitz, G. et al. (2009) *Maturitas* 63:253-6. Tahakata, C., Miyoshi, Y., Irahara, N., Taguchi, T., Tamaki, Y., Noguchi, S. (2007) *Cancer Lett* 250:229-36. One study suggested that AdipoR1 is expressed at higher levels in pre-invasive breast cancer (DCIS) than in invasive lesions. Pfeiler, G., Hudelist, G., Wulfing, P. Mattsson, B., Konigsberg, R., Kubista, E. et al. (2010) *Gynecol Oncol* 117:134-8. Between the two receptor types, AdipoR1 appears to play a more definite role in breast cancer as adiponectin-dependent anti-proliferative effects are abolished by siRNA knockdown of AdipoR1; cell lines expressing AdipoR2, but lacking AdipoR1 do not respond to adiponectin with growth inhibition. Nakayama, S., Miyoshi, Y. Ishihara, H., Noguchi, S. (2008) *Breast Cancer Res Treat* 112:405-10. Grossmann, M E., Nkhata, K J., Mizuno, N K., Ray, A., Cleary, M P. (2008) *Br J Cancer* 98:370-9.

Numerous epidemiological and experimental studies provided evidence linking obesity with the increased risk of development of different malignancies, including breast, colorectal, prostate and endometrial cancers. Maiti B, et al. *Breast Cancer Res Treat* 2010, 121(2):479-83, Vona-Davis L, et al. *Obes Rev* 2007, 8(5):395-408, Calle E E and Thun M J *Oncogene* 2004, 23(38):6365-6378, Pischon T, et al. *Proc Nutr Soc* 2008, 67(2):128-145. In addition, a calorie-rich diet has been shown to induce inflammatory responses in microglia cells, which potentially can promote development of brain neoplasms. Velloso L A, *Arq Bras Endocrinol Metabol* 2009, 53(2):151-158, Reynes G et al. *J Neurooncol* 2020, 102(1):35-41.

In obese individuals, especially in those with high visceral fat content, adiponectin levels are low. Brochu-Gaudreau K, et al. *Endocrine* 2010, 37(1):11-32. Many epidemiological studies demonstrated a link between low adiponectin and elevated risk of cancer development or presence of more aggressive neoplasms. Chen X and Wang Y, Adiponectin and breast cancer, *Med Oncol* 2010, 28(4):1288-1295, Brochu-Gaudreau K, et al. *Endocrine* 2010, 37(1):11-32, Pfeiler G et al., *Maturitas* 2009, 63(3):253-256. The mechanism underlying adiponectin signaling and cancer prevention is not clear, but it could involve induction of intracellular metabolic changes similar to those produced by calorie restriction, i.e., activation of intracellular signals such as AMPK and inhibition of growth and survival pathways Brochu-Gaudreau K, et al. *Endocrine* 2010, 37(1):11-32, Pfeiler G et al., *Maturitas* 2009, 63(3):253-256. Thus, pharmacological activation of adiponectin signaling in obese individuals that are refractory to lifestyle modifications could help to restore beneficial pathways normally controlled by this hormone.

Several studies support the notion that full length adiponectin or the globular domain of adiponectin (gAd) can produce various effects on cancer cells. In many different cancer cell lines (breast MCF-7, MDA-MB-231, T47D; colorectal HT-29, CaCO2, SW480; prostate PC3) adiponectin activated AMPK. Kornet A, et al. *J Clin Endocrinol Metab* 2007, 92(3):1041-1048, Dieudonne M N, et al. *Biochem Biophys Res Commun* 2006, 345(1):271-279, Williams C J et al. *Endocr Relat Cancer* 2008, 15(1):289-299, Zakikhani M, et al. *Cancer Prev Res (Phila)* 2008, 1(5):369-375. Adiponectin either reduced or did not affect ERK1/2 in MCF-7 or MDA-MB-231 cells, but stimulated the pathway in some colorectal cancer cell lines. Grossmann M E et al, *Br J Cancer* 2008, 98(2):370-379, Dieudonne M N, et al. *Biochem Biophys Res Commun* 2006, 345(1):271-279, Williams C J et al. *Endocr Relat Cancer* 2008, 15(1):289-299. Akt was inhibited by adiponectin in MDA-MB-231 breast cancer cells, but activated in prostate cancer cells LNCaP. Kim K Y et al. *Cancer Res* 2009, 69(9):4018-4026, Barb D et al., *Endocr Relat Can-* cer 2007, 14(4):995-1005. Moderate STAT3 stimulation by adiponectin was noted in MDA-MB-231 cells, while the transcription factor was inhibited in DU145 prostate cancer cells. Grossmann M E et al, *Br J Cancer* 2008, 98(2):370-379, Miyazaki T et al., *Biochem Biophys Res Commun* 2005, 333(1):79-87.

Although full size adiponectin or its globular domain have been shown to exhibit positive effects on various cells and tissues, the development of this cytokine into an acceptable pro-drug is pharmacologically and economically disadvantageous. Instead, small peptides or peptidomimetics based on the minimal adiponectin/adiponectin receptor-activating domain should constitute appropriate leads for drug development. Such adiponectin receptor agonists should be equipped with enhanced specificity, low toxicity, high stability, superior bioavailability parameters, and low production costs. The present invention addresses and meets these needs.

SUMMARY

Compounds of the invention are useful as adiponectin receptor agonists.

According to the invention, a compound of formula I is provided:

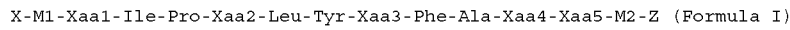

wherein SEQ ID NO:1 is Xaa1-Ile-Pro-Xaa2-Leu-Tyr-Xaa3-Phe-Ala-Xaa4-Xaa5, wherein:
(a) Xaa1 is Asn or a non-natural amino acid;
(b) Xaa2 is Gly or a non-natural amino acid;
(c) Xaa3 is Tyr or a non-natural amino acid;
(d) Xaa4 is Tyr or a non-natural amino acid;
(e) Xaa5 is no amino acid, β-Ala or β-AlaNH$_2$;
provided, at least one of Xaa1, Xaa2, Xaa3, or Xaa4 is a non-natural amino acid;
X is an optionally present
1-10 amino acid peptide,
polymer molecule,
lipophilic compound or
peptide transduction domain;
Z is an optionally present
1-10 amino acid peptide,
polymer molecule,
lipophilic compound or
peptide transduction domain;
M1 is an optionally present single bond or a linking group; and
M2 is an optionally present single bond or a linking group;
wherein, when the compound of formula I comprises a C-terminal amino acid, said C-terminal amino acid is optionally amidated;
or a salt thereof.

According to some embodiments, Xaa1 is D-Asn and Xaa4 is D-Ser.

According to some embodiments, Xaa2 is Nva.

According to some embodiments, Xaa3 is D-Ser.

According to some embodiments, Xaa2 is Nva and Xaa3 is D-Ser.

According to some embodiments, Xaa1 is D-Asn, Xaa2 is Nva, Xaa3 is D-Ser, and Xaa4 is D-Ser.

According to some embodiments, Xaa5 is β-Ala or β-AlaNH$_2$.

Provided is a compound according to any one of the previous embodiments wherein the compound has the formula:

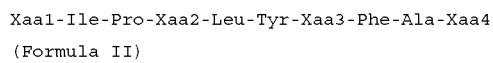

Xaa1-Ile-Pro-Xaa2-Leu-Tyr-Xaa3-Phe-Ala-Xaa4

(Formula II)

wherein the C-terminal amino acid is optionally amidated, or a salt thereof.

According to some embodiments, the compound of Formula I, or a salt thereof, is selected from the group consisting of:

ADP 355:

(SEQ ID NO: 3)
D-Asn-Ile-Pro-Nva-Leu-Tyr-D-Ser-Phe-Ala-D-Ser;

ADP 355-β-Ala:

(SEQ ID NO: 4)
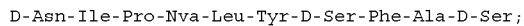
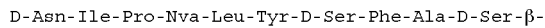
-continued
Ala;

ADP 355-β-AlaNH$_2$:

(SEQ ID NO: 5)
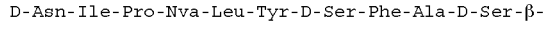
AlaNH$_2$;
and

ADP 355-NH$_2$:

(SEQ ID NO: 6)
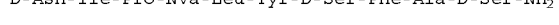

Provided is a method of treating an individual suffering from a cellular proliferative disorder, comprising administering to the individual an effective amount of at least one compound of formula I, or a pharmaceutically acceptable salt thereof. According to some embodiments, the cellular proliferative disorder is selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy and non cancerous lymphocellular proliferative disorders. According to some embodiments, the cellular proliferative disorder is cancer. In preferred embodiments, the cancer is selected from the group consisting of ovarian cancer, cervical cancer, breast cancer, prostate cancer, testicular cancer, lung cancer, renal cancer, colorectal cancer, skin cancer, brain cancer and leukemia. In further preferred embodiments, the leukemia is selected from the group consisting of acute myeloid leukemia, chronic myeloid leukemia, acute lymphoid leukemia, and chronic lymphoid leukemia. According to further embodiments, the cancer is selected from the group consisting of breast cancer and glioblastoma.

Also provided is a method of treating an individual suffering from a cellular proliferative disorder, particularly cancer, comprising administering to said individual an effective amount of at least one compound according to formula I, or a pharmaceutically acceptable salt thereof, either alone, or in combination with a pharmaceutically acceptable carrier.

The invention is also directed to the use in medicine of a compound according to formula I, or a pharmaceutically acceptable salt thereof.

The invention is also directed to the use of a compound according to formula I, or a pharmaceutically acceptable salt thereof, in the preparation of a medicament for treatment of a cellular proliferative disorder, particularly cancer.

The invention is also directed to a compound according to formula I, or a pharmaceutically acceptable salt thereof, for use in the preparation of a medicament for treatment of a cellular proliferative disorder, particularly cancer.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

BRIEF DESCRIPTION OF THE DRAWINGS

Embodiments of the present invention will now be described, by way of example only, with reference to the attached Figures.

FIG. 2 illustrates the effect of ADP 355-NH$_2$ (D-Asn-Ile-Pro-Nva-Leu-Tyr-D-Ser-Phe-Ala-D-Ser-NH$_2$; SEQ ID NO: 6) on the growth of cancer cells in vitro.

DETAILED DESCRIPTION

Figure 1A:
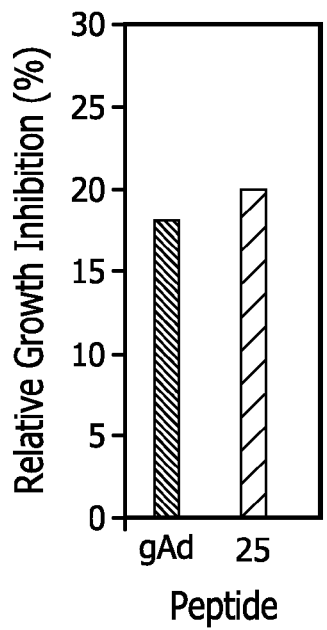
FIG. 1A illustrates the growth inhibitory effect of adiponectin peptide "25" i.e. ADP 25-βAlaNH$_2$ (Asn-Ile-Pro-Gly-Leu-Tyr-Tyr-Phe-Ala-Tyr-βAlaNH$_2$; SEQ ID NO: 7) on the growth of MCF7 cells. The effect of the entire globular domain of adiponectin (gAd) is included for comparison. The data are averages from 3 different assays and represent average results+/−SE and were analyzed by Student t-test, $p<0.05$.

As discussed supra, although full size adiponectin or its globular domain have been shown to exhibit positive effects on various cells and tissues, the development of this cytokine into an acceptable pro-drug is pharmacologically and economically disadvantageous, due to its large size. The inventors have discovered the minimal adiponectin/adiponectin receptor activating domain. This has permitted the design of small peptides or peptidomimetics based on that minimal domain, that act as adiponectin receptor agonists, exhibit high specificity and low toxicity, and can be manufactured at low cost.

The compounds of the invention are believed to inhibit the proliferation of tumor cells, and for some compounds, induce cell death. The compounds are believed effective against a broad range of malignancies, including but not limited to the following: ovarian cancer, breast cancer, prostate cancer, lung cancer, renal cancer, colorectal cancer, brain cancer and leukemia.

The compounds are also believed useful in the treatment of non-cancer cellular proliferative disorders, including but not limited to the following: hemangiomatosis in newborn, secondary progressive multiple sclerosis, chronic progressive myelodegenerative disease, neurofibromatosis, ganglion-euromatosis, keloid formation, Paget's disease of the bone, fibrocystic disease of the breast, uterine fibroids, Peyronie's disease, Dupuytren's disease, restenosis and cirrhosis.

I. DEFINITIONS

As used in the specification and the appended claims, the singular forms "a," "an" and "the" include plural referents unless the context clearly dictates otherwise.

The expressions "treat" and "treatment" and grammatical equivalents thereof mean administration of a substance to a subject with the purpose to cure, alleviate, relieve, remedy, prevent or ameliorate a disorder, or a disease state secondary to the disorder.

As used herein, "adiponectin" means a polypeptide that is primarily derived from adipocytes and is an ortholog of the human adiponectin sequence (Genbank accession No. Q15848, residues 1-244) shown employing the one-letter amino acid code in SEQ ID NO: 8:

```
MLLLGAVLLL LALPGHDQET TTQGPGVLLP LPKGACTGWM AGIPGHPGHN GAPGRDGRDG 70         80         90        100        110        120
TPGEKGEKGD PGLIGPKGDI GETGVPGAEG PRGFPGIQGR KGEPGEGAYV YRSAFSVGLE 130        140        150        160        170        180
TYVTIPNMPI RFTKIFYNQQ NHYDGSTGKF HCNIPGLYYF AYHITVYMKD VKVSLFKKDK 190        200        210        220        230        240
AMLFTYDQYQ ENNVDQASGS VLLHLEVGDQ VWLQVYGEGE RNGLYADNDN DSTFTGFLLY

HDTN
```

As used herein, "adiponectin variant" means a polypeptide that is functionally similar to adiponectin but contains modifications relative to a naturally-occurring adiponectin sequence.

As used herein, "globular domain" means, in the context of adiponectin, the C1q/TNF-a-like domain and not including the collagen domain. This region can include but is not limited to residues 108-244 relative to human adiponectin (SEQ ID NO: 9).

"Peptides" are defined herein as organic compounds comprising a chain of two or more amino acids covalently joined by peptide bonds. Peptides may be referred to with respect to the number of constituent amino acids, i.e., a dipeptide contains two amino acid residues, a tripeptide contains three, etc. A "peptide" as used in the presently claimed invention is intended to refer to a moiety with a molecular weight of less than 10,000 Daltons.

As used herein, "peptidomimetic" means a small protein-like chain designed to mimic a peptide. A peptidomimetic may be a backbone modified peptide, any polyamide or other polymeric structure resembling peptides, peptides containing non-natural amino acid residues or a peptide derivative.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, norvaline, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "hydrophobic residues" and grammatical equivalents means valine, isoleucine, leucine, methionine, phenylalanine, tyrosine, tryptophan, and functional equivalents thereof.

The term "polar residues" and grammatical equivalents means aspartic acid, asparagine, glutamic acid, glutamine, lysine, arginine, histidine, serine, and functional equivalents thereof.

The term "peptide bond" means a covalent amide linkage formed by loss of a molecule of water between the carboxyl group of one amino acid and the amino group of a second amino acid.

The term "peptide backbone" means the chain of atoms of a peptide comprising the carboxamide groups that are the peptide bonds together with the atoms of the amino acids that link the carboxyl and amino groups of the amino acid (usually the α-carbon of an α-aminoacid).

The term "side chain" means groups that are attached to the peptide backbone, and typically refers to the group attached to the α-carbon of an α-amino acid. For example, for the side chains of the proteinogenic amino acids include: methyl (alanine), hydroxymethyl (swine), benzyl (phenylalanine), mercaptomethyl (cysteine), and carboxymethyl (aspartic acid).

The term "derivative" as applied to compounds comprising a peptide chain means a compound wherein one or more of the amino, hydroxyl, or carboxyl groups in a side chain of the peptide, or the terminal amino or carboxyl groups, is modified to a derivative functional group. An amino group may be derivatized as an amide (such as an alkyl carboxamide, acetamide), a carbamate (such as an alkyl carbamate, e.g. methyl carbamate or t-butylcarbamate), or a urea. A hydroxyl group may be derivatized as an ester (such as an alkanoate, e.g. acetate, propionate, or an arenecarboxylate, e.g. benzoate), a carbamate (such as an alkyl carbamate, e.g. methyl carbamate), a carbonate (such as an alkyl carbonate, e.g. ethyl carbonate. A carboxyl group may be derivatized as an ester (such as an alkyl ester, e.g. ethyl ester) or an amide (e.g. primary carboxamide, an N-alkyl secondary carboxamide, or an N,N-dialkylcarboxamide). The person skilled in the art will appreciate that derivatives of the peptide will be expected to result in retention of the properties of the parent peptide, either because the incorporation of the derivative group does not change the properties of the peptide, or the derivatizing group is removed in vivo (e.g. via metabolism). Preferred embodiments of the invention are those wherein three or fewer of the amino, carboxyl, and hydroxyl groups, and preferably two or fewer, or one or none, are modified to a derivative functional group. The term "derivative" also includes salts, includes salts of derivatives.

"Natural amino acid" is used to refer to an amino acid which exists in nature. As used herein, amino acids are represented by the full name thereof, by the three-letter code, as well as the one-letter code corresponding thereto, as shown in Table I below. The structure of amino acids and their abbreviations can be found in the chemical literature, such as in Stryer, 1988, "Biochemistry", 3$^{rd}$ Ed., W. H. Freeman & Co., NY, N.Y.

TABLE I

Natural Amino Acids

| Full Name | Three-Letter Code | One-Letter Code |
|---|---|---|
| Alanine | Ala | A |
| Arginine | Arg | R |
| Asparagine | Asn | N |
| Aspartic Acid | Asp | D |
| Cysteine | Cys | C |
| Cystine | Cys-Cys | C-C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

"Non-natural amino acid" is used to refer to an amino acid which does not exist on its own in nature, but rather, has been synthesized or created by man. Examples of non-natural amino acids include iodinated tyrosine, methylated tyrosine, glycosylated serine, glycosylated threonine, azetidine-2-carboxylic acid, 3,4-dehydroproline, perthiaproline, canavanine, ethionine, norleucine, selenomethionine, animohexanoic acid, telluromethionine, homoallylglycine, and homopropargylglycine. D-amino acids are also examples of non-natural amino acids.

"Nva" corresponds to the non-natural amino acid norvaline, also known as 2(L)-aminopentanoic acid. "NvaNH$_2$" corresponds to 2(L)-aminopentanamide. "Acp" corresponds to the non-natural amino acid 6-aminocaproic acid, also known as 6-amino-hexanoic acid. "AcpNH$_2$" corresponds to 6-aminocapramide, also known as 6-amino-hexanamide. "Dpr(Ac)" corresponds to N2(3)-acetyl-diaminopropionic acid. "Dbu" corresponds to 2,4-diaminobutyric acid. "Glc" corresponds to glucose. "βGlc" corresponds to beta-glucose. "Serβ(Glc)" corresponds to serine glycosylated with a beta-glucosyl residue on the alcohol hydroxyl group. "Thr(NAcGal)" corresponds to threonine glycosylated with an N-acetyl galactosaminyl residue on the alcohol hydroxyl group. "Tyr (I$_2$)" corresponds to 3,5-diiodotyrosine. "N-MeArg" corresponds to N-methyl-arginine. "βAla" corresponds to beta-alanine, also known as 3-aminopropanoic acid. "βAlaNH$_2$" corresponds to the amide derivative of beta-alanine, also known as 3-aminopropanamide. "(D)-Ser" corresponds to D-serine. "Apa" corresponds to aminopentanoic acid. "AlloThr" corresponds to allo-threonine, also known as (2S,3S)-2-amino-3-hydroxybutanoic acid. "3Hyp" corresponds to 3-hydroxyproline. "4Hyp" corresponds to 4-hydroxyproline.

As used herein, the term "hydroxylated acyclic amino acid" refers to an acyclic amino acid that contains at least one alcohol hydroxyl group in its structure. Preferred, but non-limiting, examples of hydroxylated acyclic amino acid are serine, (D)-serine, threonine, (D)-threonine, (L)-allo-threonine, (D)-allo-threonine, (L)-isoserine, (D)-isoserine, (L)-β-homoserine, (D)-β-homoserine, (L)-homoserine, and (D)-homoserine.

As used herein, the term "aliphatic amino acid" refers to an amino acid which carbon chain is aliphatic in nature. Non-limiting examples of aliphatic amino acids are alanine, arginine, asparagine, aspartic acid, cysteine, glutamic acid, glutamine, glycine, isoleucine, leucine, lysine, methionine, proline, serine, threonine, valine, Nva, NvaNH$_2$, Acp, AcpNH$_2$, Dpr(Ac), Dbu, N-MeArg, βAla, βAlaNH$_2$, Apa, and AlloThr. Preferred aliphatic amino acids within the present application are βAla, βAlaNH$_2$, Acp and AcpNH$_2$.

The term "peptide transduction domain" is used to indicate a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be a peptide chain, an amino acid, or any group having at least two functional groups and capable of forming covalent bond to each of the two peptide chains.

An "acetylated amino acid" as used herein refers to an amino acid having an acetyl moiety in its side chain.

The term "cellular proliferative disorder" means a disorder wherein unwanted cell proliferation of one or more subsets of cells in a multicellular organism occurs. In some such disorders, cells are made by the organism at an atypically accelerated rate.

As used herein, "isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as a host cell for example.

As used herein, "naturally occurring" or "wild type" or "wt" or "native" and grammatical equivalents thereof mean an amino acid sequence or a nucleotide sequence that is found in nature, including allelic variations. In a preferred embodiment, the wild type sequence means the most prevalent human sequence. However, the wild type adiponectin nucleic acids and proteins may be a less prevalent human allele or adiponectin nucleic acids and proteins from any number of organisms, including but not limited to rodents (rats, mice, hamsters, guinea pigs, etc.), primates, and farm animals (including sheep, goats, pigs, cows, horses, etc.).

"Biologically active," as used herein with respect to a peptide of the invention, means that the peptide of the invention have the ability to bind and act as an antagonist to a adiponectin receptor. The term "inhibit," as used herein, means to suppress or block an activity or function by at least about ten percent relative to a control value. Preferably, the activity is suppressed or blocked by 50% compared to a control value, more preferably by 75%, and even more preferably by 95%.

"Medical intervention", as used herein, means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human.

The language "effective amount" or "therapeutically effective amount" refers to a nontoxic but sufficient amount of the composition used in the practice of the invention that is effective to promote the required growth arrest or killing of cancer cells in a subject, or is effective to treat a weight-loss nutritional disorder in a subject, or is effective to treat osteoporosis in a subject. The desired treatment may be prophylactic and/or therapeutic. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as a compound of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

As used herein with respect to formulations, the term "additional ingredients" includes, but is not limited to, one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents and pharmaceutically acceptable polymeric or hydrophobic materials. Other "additional ingredients" that may be included in the pharmaceutical compositions used in the practice of the invention are known in the art and described, for example in Remington's Pharmaceutical Sciences (Genaro, ed. Mack Publishing Co., 1985, Easton, Pa.), which is incorporated herein by reference.

"Container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions can contain information pertaining to the compound's ability to perform its intended function, e.g., causing growth arrest or death of cancerous cells in a subject. "Applicator," as the term is used herein, is used to identify any device including, but not limited to, a hypodermic syringe, a pipette, and the like, for administering the compounds and compositions used in the practice of the invention

II. COMPOUNDS OF THE INVENTION

In one aspect of the invention, there is provided a compound of the formula I:

```
X-M1-Xaa1-Ile-Pro-Xaa2-Leu-Tyr-Xaa3-Phe-Ala-Xaa4-Xaa5-M2-Z (I)
``` wherein SEQ ID NO:1 is Xaa1-Ile-Pro-Xaa2-Leu-Tyr-Xaa3-Phe-Ala-Xaa4-Xaa5, wherein:

(a) Xaa1 is Asn or a non-natural amino acid;

(b) Xaa2 is Gly or a non-natural amino acid;

(c) Xaa3 is Tyr or a non-natural amino acid;

(d) Xaa4 is Tyr or a non-natural amino acid;

(e) Xaa5 is no amino acid, β-Ala or β-Ala$NH_2$;

provided, at least one of Xaa1, Xaa2, Xaa3, or Xaa4 is a non-natural amino acid;

X is an optionally present
1-10 amino acid peptide,
polymer molecule,
lipophilic compound or
peptide transduction domain;

Z is an optionally present
1-10 amino acid peptide,
polymer molecule,
lipophilic compound or
peptide transduction domain;

M1 is an optionally present single bond or a linking group; and

M2 is an optionally present single bond or a linking group;

wherein, when the compound of formula I comprises a C-terminal amino acid, said C-terminal amino acid is optionally amidated;

or a salt thereof.

According to some embodiments, Xaa1 is D-Asn and Xaa4 is D-Ser.

According to some embodiments, Xaa2 is Nva.

According to some embodiments, Xaa3 is D-Ser.

According to some embodiments, Xaa2 is Nva and Xaa3 is D-Ser.

According to some embodiments, Xaa1 is D-Asn, Xaa2 is Nva, Xaa3 is D-Ser, and Xaa4 is D-Ser.

According to some preferred embodiments, the compound of formula I is selected from the group consisting of ADP355, ADP355-βAla, ADP355-βAla$NH_2$ and ADP355-$NH_2$; and salts thereof.

According to some embodiments, X or Z is a 1-10 amino acid peptide. In some embodiments, the X or Z peptide comprises 9 amino acids. In further embodiments, the peptide comprises 8 amino acids. In yet further embodiments, the peptide comprises 7 amino acids. In yet further embodiments, the peptide comprises 6 amino acids. In yet further embodiments, the peptide comprises 5 amino acids. In yet further embodiments, the peptide comprises 4 amino acids. In yet further embodiments, the peptide comprises 3 amino acids. In yet further embodiments, the peptide comprises 2 amino acids. In yet further embodiments, the peptide comprises 1 amino acid. The length of the peptides and identity of the substituent amino acids comprising the X and Z peptides, are independently selected.

According to some embodiments, X or Z is a polymer molecule, a lipophilic compound or an peptide transduction domain. In some embodiments, the polymer is a linear or branched polyethylene glycol. In further embodiments, the polymer has a molecular weight of from 1 kDa to 200 kDa. In yet further embodiments, the polymer has a molecular weight of from 2 kDa to 95 kDa. In yet further embodiments, the polymer has a molecular weight of from 5 kDa to 80 kDa. In yet further embodiments, the polymer has a molecular weight of from 12 kDa to 60 kDa, such as 1240 kDa, 2040 kDa, 5 kDa, 12 kDa or 20 kDa. The X and Z polymer molecules are independently selected.

According to some embodiments, Xaa5 is β-Ala. According to some embodiments, Xaa5 is β-AlaNH$_2$. According to some embodiments, Xaa5 is no amino acid.

According to some embodiments, the polymer molecule is methoxyl PEG maleimide (mPEG(MAL)), methoxyl PEG forked maleimide (mPEG2(MAL)), methoxyl PEG ortho-pyridyldisulfide (mPEG-OPSS), PEG-vinylsulphone, or ortho-pyridyldisulfide-PEG-hydrazide (OPSS-PEG-hydrazide) in combination with methoxyl PEG aldehyde (mPEG-ALD). In a further embodiment the polymer molecule is selected from the group consisting of 5k-mPEG (MAL), 20k-mPEG(MAL), 40k-mPEG2(MAL), 5k-mPEG-OPSS, 10k-mPEG-OPSS, 20k-mPEG-OPSS, or OPSS-PEG$_2$k-hydrazide in combination with mPEG$_{30}$ kD-ALD.

One of skill in the art will appreciate that when X is not present, M1 will not be present either.

One of skill in the art will appreciate that when Z is not present, M2 will not be present either.

One of skill in the art will appreciate that if the compound of Formula I has a C-terminus which comprises an amino acid, for example wherein the C-terminus comprises Z (if present and comprises a peptide or a transduction domain), Xaa5 (if present) or Xaa4, that amino acid is optionally amidated.

One of skill in the art will appreciate that a peptide (for example a dipeptide having two amino acids Xaa1 and Xaa2) can be represented as:
H-Xaa1-Xaa2-OH
wherein H is part of the free amino terminus of the peptide and OH is part of the free carboxyl terminus of the peptide;
or the peptide can be represented as:
Xaa1-Xaa2
wherein the H is part of the free amino terminus of the peptide and the OH that is part of the free carboxyl terminus of the peptide are not shown in the formula for the peptide, but are understood to be present.

Methods of Covalently Linking X or Z when X or Z is a Lipophilic Compound.

The amino acid Xaa1, Xaa5 or Xaa4 when Xaa5 is zero amino acid may be conjugated to a lipophilic compound comprising X or Z either directly or by use of a linker. The lipophilic compound may be a natural compound such as a saturated or unsaturated fatty acid, a fatty acid diketone, a terpene, a prostaglandin, a vitamin, a carotenoid or steroid or a synthetic compound such as a carbon acid, an alcohol, an amine and sulphonic acid with one or more alkyl-, aryl-, alkenyl-, or other multiple unsaturated compounds. The conjugation between the amino acid and the lipophilic compound, optionally through a linker may be done according to methods known in the art, e.g. as described by Bodanszky in Peptide Synthesis, John Wiley, New York, 1976 and in WO 96/12505.

X or Z is a Polymer Compound.

To effect covalent attachment of the polymer molecule to an amino acid, the hydroxyl end groups of the polymer molecule must be provided in activated form, i.e. with reactive functional groups (for example primary amino groups, hydrazide (HZ), thiol, succinate (SUC), succinimidyl succinate (SS), succinimidyl succinamide (SSA), succinimidyl proprionate (SPA), succinimidyl carboxymethylate (SCM), benzotriazole carbonate (BTC), N-hydroxysuccinimide (NHS), aldehyde, nitrophenylcarbonate (NPC), and tresylate (TRES). Specific examples of activated PEG polymers include the following linear PEGs: NETS-PEG (e.g. SPA-PEG, succinimidyl succinate proprionate-PEG (SSPA-PEG), SBA-PEG, SS-PEG, SSA-PEG, succinimidyl carbonate-PEG (SC-PEG), succinimidyl glutarate-PEG (SG-PEG), and SCM-PEG and NOR-PEG), BTC-PEG, epoxide-PEG (EPDX-PEG), isocyanate-PEG (NCO-PEG), NPC-PEG, carbonylimidazole-PEG (CDI-PEG), aldehyde-PEG (ALD-PEG), TRES-PEG, VS-PEG, iodo-PEG, and maleimide-PEG (MAL-PEG), and branched PEGs such as PEG2-NHS and those disclosed in U.S. Pat. No. 5,932,462 and U.S. Pat. No. 5,643,575, both of which references are hereby incorporated by reference in their entirety. The PEGylation may be directed towards specific attachment groups, e.g. the N-terminal amino group (U.S. Pat. No. 5,985,265). Furthermore, the conjugation may be achieved in one step or in a stepwise manner (e.g. as described in WO 99/55377).

a. Preparation of Compounds of the Invention

The compounds of the invention may be prepared by methods known to the person skilled in the art of peptide and organic synthesis.

Peptides of the present invention may be natural peptides, recombinant peptides or synthetic peptides. They may also be chemically synthesized, using, for example, solid phase synthesis methods. Preferred methods of synthesis of compounds of formula I are set forth in Examples 1 and 2 herein. Additionally, peptide transduction domains appended to peptides of the invention may be natural or synthetic peptides, and may be either prepared by isolation from natural sources or may be synthesized.

The peptides of the present invention may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage reagents, e.g., trifluoroacetic acid (TFA), HCl in dioxane, boron tris-(trifluoracetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

In an embodiment, the peptide synthesis method may follow Merrifield solid-phase procedures. See Merrifield, *J. Am. Chem. Soc.,* 1963, 85, 2149-54 and *Science,* 1965, 50, 178-85. Additional information about the solid phase synthetic procedure can be obtained from the treatises *Solid Phase Peptide Synthesis: A Practical Approach* by E. Atherton and R. C. Sheppard (Oxford University Press, 1989, *Solid phase peptide synthesis*, by J. M. Stewart and J. D. Young, (2nd edition, Pierce Chemical Company, Rockford, 1984), and the review chapters by R. Merrifield in *Advances in Enzymology* 32:221-296, edited by F. F. Nold (Interscience Publishers, New York, 1969) and by B. W. Erickson and R. Merrifield in *The Proteins* Vol. 2, pp. 255 et seq., edited by Neurath and Hill, (Academic Press, New York, 1976). Peptide synthesis may follow synthetic techniques such as those set forth in Fields et al., *Introduction to Peptide Synthesis*, in *Current Protocols in Molecular Biology* (Chapter 11, Unit 11.15; John Wiley and Sons, 2008) and Amblard et al. (2006, Molecular Biotechnology, 33:239-254).

The synthesis of peptides by solution methods is described in The Proteins, Vol. 11, edited by Neurath et al. ($3^{rd}$ Edition, Academic Press 1976). Other general references to the synthesis of peptides include: *Peptide Synthesis Protocols*, edited by M. W. Pennington and Ben M. Dunn (Humana Press 1994), *Principles of Peptide Synthesis*, by Miklos Bodanszky ($2^{nd}$ edition, Springer-Verlag, 1993), and *Chemical Approaches to the Synthesis of Peptides and Proteins* by Paul Lloyd-Williams, F. Albericio, E. Giralt (CRC Press 1997), and *Synthetic Peptides: A User's Guide*, edited by G. Grant (Oxford University Press, 2002).

Alternatively, peptides may be prepared utilizing recombinant DNA technology, which comprises combining a nucleic acid encoding peptides of formula I in a suitable vector, inserting the resulting vector into a suitable host cell, recovering the peptide subsequently produced by the host cell, and purifying the polypeptide recovered. The required techniques of recombinant DNA and protein technology are known to the ordinary skilled artisan. General methods for the cloning and expression of recombinant molecules are described in *Molecular Cloning* by Sambrook et al. (Cold Spring Harbor Laboratories, Second Ed., 1989) and in *Current Protocols in Molecular Biology* by Ausubel (Wiley and Sons, 1987).

The nucleic acid encoding a desired peptide may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

Promoters that may be used in the synthesis of compounds of the present invention include both constitutive promoters and inducible promoters. The promoters may be prokaryotic or eukaryotic, depending on the host.

The compounds of the invention, whether prepared by chemical synthesis or recombinant DNA technology, may be purified using known techniques, for example preparative HPLC, FPLC, affinity chromatography, as well as other chromatographic methods. Isolated compounds may then be assessed for biological activity according to the methods described herein, as well as by any methods known to the skilled artisan.

For synthetic techniques, peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent.

Linking Groups (M1 and M2)

The linking group (M1 or M2) for coupling X or Z in a compound of formula I may be any moiety that is at least bifunctional, provided that the resulting link between X or Z and the N-terminal or C-terminal amino acid or non-natural amino acid is stable. Suitable linking groups include bi- and multi-functional alkyl, aryl, aralkyl or peptidic moieties, alkyl, aryl or aralkyl aldehydes acids esters and anhydrides, sulfhydryl or carboxyl groups, such as maleimido benzoic acid derivatives, maleimido propionic acid derivatives and succinimido derivatives or may be derived from cyanuric bromide or chloride, carbonyldiimidazole, succinimidyl esters or sulphonic halides and the like (Fischer et al., U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups.

Optionally the linker group is selected so as to be sufficiently labile (e.g., to enzymatic cleavage by an enzyme present in the targeted tissue) so that it is cleaved following transport of a peptide of the invention, thereby releasing the peptide. Exemplary labile linkages are described in Low et al., U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

The examples provided below are intended to be illustrative and not comprehensive. Thus, the examples below illustrate the case where the bonds between the M1 or M2 group and the peptides are amide bonds, but the person skilled in the art would appreciate that the link may be formed by means of any functional groups capable of forming bonds between the Xaa1 or Xaa5 and a —C(=O)— group of the terminal (or other) carboxyl group (or the terminal, or other —NH— group, or any other functional group of X or Z respectively).

If the link formed by the linking group M1 is between the Xaa1 and a carboxyl group of X (for example if X is a tagging element, the terminal carboxyl group of a peptidic tagging element or the terminal carboxyl group of a molecule), any amino acid (including, but not restricted to, α-amino acids including, but not restricted to, the proteinogenic amino acids) or peptide chain may form the link between Xaa1 and X.

Examples of suitable linking groups M1 for linking Xaa1 and a carboxyl group of X include:
—NH—CH(R)—C(=O)—, wherein R is a side chain of a proteinogenic amino acid;
a peptide chain; and
—NH—Z3$_m$—C(=O)—, wherein:
  m is one or greater, preferably one to three,
  each —Z3- is selected from the group consisting of:
    a linear, branched, or cyclic aliphatic hydrocarbon, wherein one or more methylene groups are optionally replaced by —O— or —S— and one or more methine groups are optionally replaced by N;

—CH$_2$CH$_2$(OCH$_2$CH$_2$)$_n$—; wherein "n" is one or greater; and, an aromatic or heteroaromatic ring.

If the link formed by the linking group M1 is between Xaa1 and an amino group of X (for example the terminal amino group of a peptidic X or the terminal amino group of a molecular X), the link between the two peptide groups could be for example be a urea (where M1 is —C(=O)—) or any dicarboxylic acid residue (e.g. M1 is —C(=O)—(C$_1$-C$_6$) alkylene-C(=O)—).

Examples of suitable linking group M1 for linking Xaa1 and an amino group of the working element include:

—C(=O)— (i.e. a urea);

—C(=O)-Pep$^1$-NH—C(=O)—NH-Pep$^2$-C(=O)—, wherein —NH-Pep$^1$-C(=O)— and —NH-Pep$^2$-C(=O)— each represent either an amino acid or a peptide chain, linked via their amino termini (or the α-amino group in the case of an amino acid) by the urea linkage —NH—C(=O)—NH—; and —C(=O)—Z3$_m$—C(=O)—, wherein:

m is one or greater, preferably one to three;

each —Z3- is selected from the group consisting of:

a linear, branched, or cyclic aliphatic hydrocarbon, wherein one or more methylene groups are optionally replaced by —O— or —S— and one or more methine groups are optionally replaced by N;

—CH$_2$CH$_2$(OCH$_2$CH$_2$)$_n$—; wherein "n" is one or greater; and, an aromatic or heteroaromatic ring.

Although the M1 group is referred to as "linking" X and Xaa1, the use of this term is not intended to imply any limitation as to the process by which the compound of formula I is synthesized. Thus it is not necessary that X and the rest of the compound of formula I be separately synthesized and then linked together. Rather, the term merely describes the structural connection between X, Xaa1, and the linking group M1 in the compound of formula I.

If the link formed by the linking group M2 is between the Xaa5 and a carboxyl group of Z (for example if Z is a tagging element, the terminal carboxyl group of a peptidic tagging element or the terminal carboxyl group of a molecule), any amino acid (including, but not restricted to, α-amino acids including, but not restricted to, the proteinogenic amino acids) or peptide chain may form the link between Xaa5 and Z.

Examples of suitable linking groups M2 for linking Xaa5 and a carboxyl group of Z include:

—NH—CH(R)—C(=O)—, wherein R is a side chain of a proteinogenic amino acid;

a peptide chain; and

—NH—Z4$_m$—C(=O)—, wherein:

m is one or greater, preferably one to three, each —Z4- is selected from the group consisting of:

a linear, branched, or cyclic aliphatic hydrocarbon, wherein one or more methylene groups are optionally replaced by —O— or —S— and one or more methine groups are optionally replaced by N;

—CH$_2$CH$_2$(OCH$_2$CH$_2$)$_n$—; wherein "n" is one or greater; and, an aromatic or heteroaromatic ring.

If the link formed by the linking group M2 is between Xaa5 and an amino group of Z (for example the terminal amino group of a peptidic Z or the terminal amino group of a molecular Z), the link between the two peptide groups could be for example be a urea (where -M2- is —C(=O)—) or any dicarboxylic acid residue (e.g. -M2- is —C(=O)—(C$_1$-C$_6$) alkylene-C(=O)—).

Examples of suitable linking group M2 for linking Xaa5 and an amino group of Z include:

—C(=O)— (i.e. a urea);

—C(=O)-Pep$^1$-NH—C(=O)—NH-Pep$^2$-C(=O)—, wherein —NH-Pep$^1$-C(=O)— and —NH-Pep$^2$-C(=O)— each represent either an amino acid or a peptide chain, linked via their amino termini (or the α-amino group in the case of an amino acid) by the urea linkage —NH—C(=O)—NH—; and —C(=O)—Z4$_m$—C(=O)—, wherein:

m is one or greater, preferably one to three;

each —Z4- is selected from the group consisting of:

a linear, branched, or cyclic aliphatic hydrocarbon, wherein one or more methylene groups are optionally replaced by —O— or —S— and one or more methine groups are optionally replaced by N;

—CH$_2$CH$_2$(OCH$_2$CH$_2$)$_n$—; wherein "n" is one or greater; and, an aromatic or heteroaromatic ring.

Although the M2 group is referred to as "linking" Xaa5 and Z, the use of this term is not intended to imply any limitation as to the process by which the compound of formula I is synthesized. Thus it is not necessary that Z and the rest of the compound of formula I be separately synthesized and then linked together. Rather, the term merely describes the structural connection between Z, Xaa5, and the linking group M2 in the compound of formula I.

Tagging Elements (X and/or Z).

The tagging element (which may be X and/or Z) is selected from the group consisting of a transduction domain and a detection label.

The compounds of the invention may or may not have the ability to cross the blood brain barrier, depending on their intrinsic properties. Determination of ability of the compounds of the invention to penetrate the blood brain barrier may be easily performed using standard techniques such as those cited in Bernacki et al., 2008, *Pharmacol. Rep.* 60 (5): 600-22.

In the case that the compound of the invention has low or nearly inexistent ability to penetrate the blood brain barrier, the activity of the compound of the invention may not be felt in receptors located in various parts of the brain. This may limit the action of the compound to those receptors located outside of the central nervous system. In that case, the compound of the invention finds use in the treatment of cancers that occur in peripheral systems, such as breast cancer, colorectal cancer, prostate cancer, pancreatic cancer, ovarian cancer, endometric cancer and lung cancer.

In the case that the compound of the invention has significant ability to penetrate the blood brain barrier, the activity of the compound may be felt in receptors located in various parts of the brain. In this case, the compound may be active against receptors located both inside and outside the central nervous system. In that case, the compound of the invention finds use in the treatment of weight-loss nutritional disorders, such as cachexia and wasting, and cancers, such as glioma, in addition to peripheral cancers such as breast cancer, colorectal cancer, prostate cancer, pancreatic cancer, ovarian cancer, endometric cancer and lung cancer.

The ability of the compound of the invention to cross the blood brain barrier may be enhanced when it comprises a transduction domain as the tagging element (X and/or Z). The transduction domain improves the ability of the construct to cross the cell membrane (see PCT Application WO 2008/070049, incorporated by reference herein in its entirety). Such transduction domain may be a peptide selected for its known membrane-crossing properties.

The property of promoting facile cellular entry is retained even when the peptide sequence is conjugated to another molecule. As a result, conjugation to such sequences can be used to facilitate delivery into cells of other peptides, such as those of formula I of the present invention. See, for example, *Handbook of Cell-Penetrating Peptides*, by Ulo Langel (Editor) (CRC Press, 2$^{nd}$ Edition, 2006). *Cell-Penetrating Peptides: Process and Applications*, by Ulo Langel (Editor) (CRC Press, 1$^{St}$ Edition, 2002); and E. L. Snyder, et al., "Cell-penetrating Peptides in Drug Delivery", *Pharm. Res.*, 2004, 21(3), 389-93.

Peptide transduction domains useful in the invention include, but are not limited to, a Tat peptide from HIV glycoprotein 120, a transportan, polyarginine, polylysine, and proline-arginine rich antibacterial peptides such as pyrrhocoricin, as set forth in U.S. Pat. No. 7,015,309, incorporated herein by reference in its entirety. In one aspect of the invention, a peptide transduction domain is polycationic.

The compounds of the invention may also benefit from the property of being easily monitored or detected in vitro or in vivo. In vitro, the monitoring or detection of the compounds of the invention would allow one skilled in the art to identify whether and/or which cells under observation contain adiponectin receptors, and to follow the binding of the compounds of the invention to such adiponectin receptor-positive cells. In vivo, the monitoring or detection of the compounds of the invention would allow one skilled in the art to determine whether/or which the tissues under observation contain adiponectin-receptor positive cells and to evaluate the biodistribution of the peptides dose in an individual. In one embodiment, the compound of the invention binds to the adiponectin receptor-positive cell and the binding is evaluated by measuring the change in a specified physical property of the compound of the invention once it binds to the cell. Non-limiting physical properties contemplated within the invention include UV-vis absorption; IR absorption; $^1$H, $^{13}$C or $^{15}$N NMR signals or relaxation; fluorescence; and magnetic properties.

The ability of detecting a compound of the invention, in either an unbound or a bound form, may be enhanced when the compound of the invention comprises a detection label as the tagging element (X and/or Z). In this case, cells that present adiponectin receptors on their surfaces may bind the peptide of the invention and the detection label may be used to monitor the binding or identify the position of the adiponectin receptor-containing cells. The method used to monitor such phenomena is dependent on the specific nature of the detection label. In the case that the detection label is a fluorescent label, fluorescent detection would be favored. In one embodiment, the compound of the invention binds to the adiponectin receptor-positive cell and the binding is evaluated by measuring the change in fluorescence of the compound of the invention upon binding to the cell.

b. Protein Transduction Domains

In some embodiments, X and/or Z may comprise a protein transduction domain. A protein transduction domain is a peptide that is capable of crossing cell membranes and of directing the transport of a peptide, protein, or molecule associated with the protein transduction domain; from the outside of a cell into the cytoplasm of the cell through the cytoplasmic membrane of the cell.

Several naturally occurring proteins have been able to enter cells easily, including the TAT protein of HIV, the antennapedia protein from Drosophila, and the VP22 protein from the herpes simplex virus. Although the mechanism of cellular entry for such proteins is not fully understood, it has been found that relatively short sequences (a protein transduction sequence or a membrane fusion sequence) in such proteins accounts for the facile cellular entry. The property of promoting facile cellular entry is retained even when the peptide sequence is conjugated to another molecule. As a result, conjugation to such sequences can be used to facilitate delivery into cells of other molecules.

Protein transduction domains have been the subject of considerable interest and investigation because of their ability, through conjugation to other compounds, to facilitate transport of the conjugated compound into the cell, and as a result a substantial body of literature has been published. See, for example, *Handbook of Cell-Penetrating Peptides*, by Ulo Langel (Editor) (CRC Press, 2$^{nd}$ Edition, 2006). *Cell-Penetrating Peptides: Process and Applications*, by Ulo Langel (Editor) (CRC Press, 1$^{st}$ Edition, 2002); E. L. Snyder, et al., "Cell-penetrating Peptides in Drug Delivery", *Pharm. Res.*, 2004, 21(3), 389-93. A. J. M. Beerens, et al., "Protein Transduction Domains and their utility in Gene Therapy", *Current Gene Therapy*, 2003, 3(5), 486-94; F. Hudecz, et al., "Medium-sized peptides as built in carriers for biologically active compounds", *Med. Res. Rev.*, 2005, 25(6), 679-736.

Examples of amino acid sequences that may be incorporated in, or used as, protein transduction domains are those shown in Table II.

TABLE II

| Examples of Protein transduction domains | |
|---|---|
| Sequence | Name and/or Source |
| Tyr Gly Arg Lys Lys Arg Arg Gln Arg Arg Arg Gly (SEQ ID NO: 10) | HIV TAT |
| Gly Arg Lys Lys Arg Arg Gln Arg Arg Pro Pro Gln Cys (SEQ ID NO: 11) | HIV TAT |
| Gly Arg Lys Lys Arg Arg Gln Arg Arg Pro Pro Gln (SEQ ID NO: 12) | HIV TAT |
| Tyr Gly Arg Lys Lys Arg Arg Gln Arg Arg Arg (SEQ ID NO: 13) | HIV TAT |
| Tyr Ala Arg Lys Ala Arg Arg Gln Ala Arg Arg (SEQ ID NO: 14) | Synthetic sequence (based on HIV TAT) |
| Tyr Ala Arg Ala Ala Ala Arg Gln Ala Arg Ala (SEQ ID NO: 15) | Synthetic sequence (based on HIV TAT) |

TABLE II -continued

Examples of Protein transduction domains

| Sequence | Name and/or Source |
|---|---|
| Tyr Ala Arg Ala Ala Arg Arg Ala Ala Arg Arg (SEQ ID NO: 16) | Synthetic sequence (based on HIV TAT) |
| Tyr Ala Arg Ala Ala Arg Arg Ala Ala Arg Ala (SEQ ID NO: 17) | Synthetic sequence (based on HIV TAT) |
| Arg Gln Ile Lys Ile Trp Phe Gln Asn Arg Arg Met Lys Trp Lys Lys (SEQ ID NO: 18) | Pantp(43-88) ("Penetratin") |
| Lys Lys Trp Lys Met Arg Arg Asn Gln Phe Trp Val Lys Val Gln Arg (SEQ ID NO: 19) | Retro-inverso pAntp (43-48) |
| Arg Arg Trp Arg Arg Trp Trp Arg Arg Trp Trp Arg Arg Trp Arg Arg (SEQ ID NO: 20) | W/R Penetratin |
| Arg Arg Met Lys Trp Lys Lys (SEQ ID NO: 21) | Pantp (52-58) |
| Arg Arg Arg Arg Arg Arg Arg (SEQ ID NO: 22) | Arginine 7-mer |
| Arg Arg Arg Arg Arg Arg Arg Arg Arg (SEQ ID NO: 23) | Arginine 9-mer |
| Asp Ala Ala Thr Arg Ser Ala Ala Ser Arg Pro Thr Glu Arg Pro Arg Ala Pro Ala Arg Ser Ala Ser Arg Pro Arg Arg Pro Val Glu (SEQ ID NO: 24) | VP22 transduction domain (*Herpes Simplex Virus 1*) |
| Gly Ala Leu Phe Leu Gly Trp Leu Gly Ala Ala Gly Ser Thr Met Gly (SEQ ID NO: 25) | GP41 fusion sequence |
| Gly Ala Leu Phe Leu Gly Phe Leu Gly Ala Ala Gly Ser Thr Met Gly Ala Trp Ser Gln Pro Lys Ser Lys Arg Lys Val (SEQ ID NO: 26) | GP41 fusion sequence. |
| Met Gly Leu Gly Leu His Leu Leu Val Leu Ala Ala Ala Leu Gln Gly Ala Trp Ser Gln Pro Lys Lys Lys Arg Lys Val (SEQ ID NO: 27) | *Caiman crocodylus* Ig(v) light chain- SN40NLS |
| Pro Leu Ser Ser Ile Phe Ser Arg Ile Gly Asp Pro (SEQ ID NO: 28) | *Hepatitis B virus* PreS2 antigen consisting of the translocation motif from residues 41-52. |
| Phe Trp Arg Gly Asp Leu Val Phe Asp Phe Gln Val (SEQ ID NO: 29) | *Hepatitis A virus* VP3 core protein. |
| Lys Phe Thr Ile Val Phe Pro His Asn Gln Lys Gly Asn Trp Lys Asn Val Pro Ser Asn Tyr His Tyr Cys Pro (SEQ ID NO: 30) | *Vesicular stomatitis virus* VSV-G peptide. |
| Ala Lys Arg Ala Arg Leu Ser Thr Ser Phe Asn Pro Val Tyr Pro Tyr Glu Asp Glu Ser (SEQ ID NO: 31) | Adenovirus fiber |
| Gly Trp Thr Leu Asn Ser Ala Gly Tyr Leu Leu Gly Lys Ile Asn Leu Lys Ala Leu Ala Ala Leu Ala Lys Lys Ile Leu (SEQ ID NO: 32) | Transportan |
| Arg Gly Gly Arg Leu Ser Tyr Ser Arg Arg Arg Phe Ser Thr Ser Thr Gly Arg (SEQ ID NO: 33) | SynB1 |
| Ala Ala Val Ala Leu Leu Pro Ala Val Leu Leu Ala Leu Leu Ala Pro (SEQ ID NO: 34) | Kaposi's sarcoma-associated herpesvirus Kaposi FGF signal sequence |
| Ala Ala Val Leu Leu Pro Val Leu Leu Ala Ala Pro (SEQ ID NO: 35) | Kaposi's sarcoma-associated herpesvirus Kaposi FGF signal sequence |
| Val Thr Val Leu Ala Leu Gly Ala Leu Ala Gly Val Gly Val Gly (SEQ ID NO: 36) | Human integrin beta3 signal sequence |
| Val Ala Tyr Ile Ser Arg Gly Gly Val Ser Thr Tyr Tyr Ser Asp Thr Val Lys Gly Arg Phe Thr Arg Gln Lys Tyr Asn Lys Arg Ala (SEQ ID NO: 37) | P3 Membrane Fusion Sequence |
| Lys Leu Ala Leu Lys Leu Ala Leu Lys Ala Leu Lys Ala Ala Leu Lys Leu Ala (SEQ ID NO: 38) | Model ambiphilic peptide |

TABLE II -continued

Examples of Protein transduction domains

| Sequence | Name and/or Source |
|---|---|
| Trp Glu Ala Lys Leu Ala Lys Ala Leu Ala Lys Ala Leu Ala Lys His Leu Ala Lys Ala Leu Ala Lys Ala Leu Lys Ala Cys Glu Ala (SEQ ID NO: 39) | KALA |
| Arg Arg Gln Arg Arg Thr Ser Lys Leu Met Lys Arg (SEQ ID NO: 40) | Synthetic (U.S. Pat. No. 6,881,825) |

Non-limiting examples of detection labels are fluorescent labels, such as cyanin derivatives (Bioconj. Chem. 1993, 4, 105-111), coumarin derivatives such as aminomethylcoumarin (Histochem. J. 1986, 8(9): 497-9), Lucifer Yellow (Invitrogen, Carlsbad, Calif.), dansyl chloride and derivatives (Methods Mol. Biol. 1994, 32: 329-34), phycobiliproteins (such as B-phycoerythrin, R-phycoerythrin and allophycocyanin; Biochem, J. 1980, 187 (2): 303-9), Oregon Green 488 (J. Lipid Res. 2003, 44 (5): 1033-1041), rhodamine derivatives (such as Rhodamine B, Rhodamine 6G, Rhodamine 123, tetramethylrhodamine, Sulforhodamine 101, and Rhodamine Red; Invitrogen, Carlsbad, Calif.), Texas Red (sulfonyl chloride version of sulforhodamine 101; Immunol. Methods 1982, 50 (2): 193-204), fluorescein (Pract. Synth. Proced. 2004, 31 (15): 2591-2593), BODIPY derivatives (FL, TR, and TMR; Chem. Rev. 2007, 107 (11): 4891-4932), carboxy SNARF-1 (Invitrogen, Carlsbad, Calif.), Cascade Blue (Invitrogen, Carlsbad, Calif.), and the family of Alexa Fluor dyes (such as Alexa Fluor 350, Alexa Fluor 488, Alexa Fluor 647, Alexa Fluor 546, Alexa Fluor 594, Alexa Fluor 660, and Alexa Fluor 680; Molecular Probes, Invitrogen, Carlsbad, Calif.).

c. Salts of Compounds of the Invention

Peptide chains typically contain acidic or basic groups (such as amine or carboxyl groups) and such groups will not necessarily be in the free base form. When referring to compounds that are peptides or compounds that contain peptide chains, the reference is intended to include salt forms of the peptide. Within the scope of the invention, therefore, are salts of compounds of formula I and the derivatives thereof. The preferred salts are pharmaceutically-acceptable salts.

The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound according to formula I by reacting, for example, the appropriate acid or base with the compound according to formula I.

d. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 1 to about 500 mg, preferably from about 7.5 to about 500 mg. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

III. ACTIVITY OF THE COMPOUNDS OF THE INVENTION

In an aspect, a compound of the invention has "full agonist activity" of the adiponectin receptor. As used herein, "full agonist activity" means that a compound of invention demonstrates agonistic activity, but does not demonstrate antagonistic activity in the dosage form recommended, with respect to adiponectin receptor both in the presence and absence of exogenous native adiponectin or other adiponectin receptor-stimulating agents.

Compounds of the invention that bind to adiponectin receptor or that bind to and stimulate some or all of the function of adiponectin receptor (adiponectin receptor agonistic activity) may be assayed using a cellular assay as set forth in detail in Example 1 herein. In an embodiment of the invention, an adiponectin receptor binding and/or agonist assay is conducted using a cell line expressing adiponectin receptor, wherein such cells are stimulated to grow as a result of treatment with adiponectin or adiponectin analogs. The skilled artisan will be aware of methods of detecting peptide-receptor binding. Western blotting and dot-blotting techniques, among others, are useful for determining the binding of a compound of the invention to adiponectin receptor. The skilled artisan will also be aware of methods of detecting and measuring cell growth. Cell counting, among other techniques, can be used to determine cell growth as a result of agonist activity of a compound of the present invention.

Other methods of measuring efficacy of compounds of the invention include, but are not limited to, receptor-binding assays, monitoring changes in downstream signaling of intracellular signaling pathways, induction of DNA and/or protein synthesis, or monitoring metabolic status of cells. Additionally, the efficacy of compounds of the invention can also be assayed in animal models, i.e., by monitoring the ability of the compounds to substitute for adiponectin in adiponectin-deficient animals, or by monitoring food intake, appetite, metabolic rates, and glucose/lipid levels in animals with obesity and insulin resistance.

IV. METHODS OF TREATMENT USING COMPOUNDS OF THE INVENTION

The compounds of the invention are useful as adiponectin receptor agonists. They bind to adiponectin receptor and agonize adiponectin receptor-mediated activity, and thus, can be used for the treatment of diseases and conditions which can benefit from an adiponectin receptor-mediated upregulation in cell signaling and growth, including conditions that are related to adiponectin deficiency or adiponectin resistance. Accordingly, compounds of the invention may be used to treat conditions including, but not limited to, proliferative disorders. The aforementioned conditions are related to, at least in part, to adiponectin deficiency and/or adiponectin resistance.

Therefore, an individual who is in need of treatment with a compound according to the invention can be an individual who is suffering from one or more proliferative disorders, among other disorders.

According to another embodiment of the invention, a method of treating an individual suffering from a cellular proliferative disorder, particularly cancer, is provided, comprising administering to said individual an effective amount of at least one compound according to formula I, or a pharmaceutically acceptable salt thereof, either alone, or in combination with a pharmaceutically acceptable carrier.

The invention is also directed to the use in medicine of a compound according to formula I, or a pharmaceutically acceptable salt thereof.

The invention is also directed to the use of a compound according to formula I, or a pharmaceutically acceptable salt thereof, in the preparation of a medicament for treatment of a cellular proliferative disorder, particularly cancer.

The invention is also directed to a compound according to formula I, or a pharmaceutically acceptable salt thereof, for use in the preparation of a medicament for treatment of a cellular proliferative disorder, particularly cancer.

Particular and preferred embodiments of this aspect of the invention are those wherein the compound of formula I used in the method of treatment, either alone or as part of a composition, or as a component of the antibody conjugate, is a particular or preferred embodiment of the compound of formula I in the description of the compounds and compositions of the invention as provided herein.

The compounds according to the invention may be administered to individuals (mammals, including animals and humans) afflicted with a cellular proliferative disorder such as cancer, malignant and benign tumors, blood vessel proliferative disorders, autoimmune disorders, and fibrotic disorders. In a particular embodiment of the invention, the individual treated is a human.

The compounds are believed effective against a broad range of malignancies, including but not limited to the following: ovarian cancer; cervical cancer; breast cancer; prostate cancer; testicular cancer; lung cancer; renal cancer; colorectal cancer; skin cancer; brain cancer; leukemia, including acute myeloid leukemia, chronic myeloid leukemia, acute lymphoid leukemia, and chronic lymphoid leukemia.

More particularly, malignancies that may be treated by the compounds, compositions and methods of the invention include, but are not limited to, the following:

cardiac cancers, including, for example sarcoma, e.g., angiosarcoma, fibrosarcoma, rhabdomyosarcoma, and liposarcoma; myxoma; rhabdomyoma; fibroma; lipoma and teratoma;

lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma;

gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma;

genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma;

liver cancers, including, for example, hepatoma, e.g., hepatocellular carcinoma; cholangiocarcinoma; hepatoblastoma; angiosarcoma; hepatocellular adenoma; and hemangioma;

bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors;

nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiforme, oligodendroglioma, schwannoma, retinoblastoma, and congenital tumors; and malignancies of the spinal cord, e.g., neurofibroma, meningioma, glioma, and sarcoma;

gynecological cancers, including, for example, cancers of the uterus, e.g., endometrial carcinoma; cancers of the cervix, e.g., cervical carcinoma, and pre-tumor cervical dysplasia; cancers of the ovaries, e.g., ovarian carcinoma, including serous cystadenocarcinoma, mucinous cystadenocarcinoma, unclassified carcinoma, granulosa-thecal cell tumors, Sertoli-Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma;

hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia;

skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers (malignancies, neoplasms) may be solid tumors that may or may not be metastatic. The term "cancer" as used herein is not limited to being of epithelial tissues only. Cancers may also occur, as in leukemia, as a diffuse tissue. Thus, the term "tumor cell", as provided herein, includes a cell afflicted by any one of the above identified disorders.

The compounds are also believed useful in the treatment of non-cancer cellular proliferative disorders, that is, cellular proliferative disorders which are characterized by benign indications. Such disorders may also be known as "cytoproliferative" or "hyperproliferative" in that cells are made by the body at an atypically elevated rate. Non-cancer cellular proliferative disorders believed treatable by compounds according to the invention include, for example: hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X-linked lymphocellular proliferative disorder (Duncan disease), post-transplantation lymphocellular proliferative disorder (PTLD), macular degeneration, and retinopathies, such as diabetic retinopathies and proliferative vitreoretinopathy (PVR)

Other non-cancer cellular proliferative disorders believed treatable by compounds according to the invention include the presence of pre-cancerous lymphoproliferative cells associated with an elevated risk of progression to a cancerous disorder. Many non-cancerous lymphocellular proliferative disorders are associated with latent viral infections such as Epstein-Barr virus (EBV) and Hepatitis C. These disorders often begin as a benign pathology and progress into lymphoid neoplasia as a function of time.

Other disorders that may be treated with compounds according to formula I include type 1 diabetes, type 2 diabetes, syndrome X, obesity, impaired glucose tolerance, insulin resistance in different organs and tissues, impaired fatty-acid oxidation in different tissues, dislipidemia, lipodystrophy/lipoatrophy, cardiovascular disease such as atherosclerosis, dyslipidemia, weight loss with or without reducing food intake, rheumatoid arthritis, Crohn's disease, systemic lupus erythematosus, Sjögren's disease, cachexia, septic shock, myasthenia gravis, post-traumatic brain damage, myocardial infarction, post-surgical brain damage, and other destructive processes related to stress or activation of the inflammatory system.

Other disorders that may be treated with compounds according to formula I are diseases, disorders or conditions caused by the expression or release of TNF-alpha in a human cell, wherein said compounds inhibit expression or release of TNF-alpha. Examples of such TNF-alpha diseases or disorders comprise inflammatory disease, circulatory disease, portal hypertension, pulmonary hypertension, allergic diseases, Crohn's disease, aumoimmune haemolytic anemia, psoriasis, hepatic disease, pancreatic disease, neurodegenerative disease, central nerve failure, toxaemia, climacteric failure, gestosis, adiposis, hyperlipidemia, hypercholesteremia, abnormal glucose tolerance, solid tumor, tumor cancer and accompanying cachexia, endocrine disease, Cretuzfeldt-Jakob disease, viral infection, post-percutaneous coronary arterioplasty, vascular hypertrophy or occlusion, post-PTCA/stenting/bypass surgery vascular reocclusion/restenosis, post-intervention vascular hypertrophy or occlusion, suppression of implantation-induced vascular failure and rejection, rejection episodes following organ or tissue transplant and autoimmune disease, side effects associated with TNF generation during neoplastic therapy and also to eliminate or ameliorate shock related symptoms associated with the treatment or prevention of graft rejection, dialytic hypotension, glaucoma, high ocular tension, myasthenia gravis, chronic defatigation, bone disease, neurological disorders, TNF-alpha induced insulin resistance, aberrant apoptosis, complications of diabetis mellitus or stress hyperglycemia, chronic obstructive pulmonary disease, chronic bronchitis and emphysema.

Inflammatory responses that may be treated with compounds according to formula I comprise diabetic complications such as retinopathy, nephropathy, neuropathy, major vascular and microvascular disorders; arthritis such as chronic rheumatoid arthritis, osteoarthritis, rheumatoid myelitis and periosteosis, postoperative/posttraumatic inflammation, swelling, pharyngitis, cystitis, pneumonia, myocarditis, cardiomyopathy, atopic dermatitis, inflammatory intestinal disease such as Crohn's disease and ulcerative colitis, meningitis, inflammatory ophthalmic disease, inflammatory pulmonary disease such as pneumonia, silicotuberculosis, pulmonary sarcoidosis, inflammatory bone disorders and pulmonary tuberculosis.

Circulatory diseases that may be treated with compounds according to formula I comprise chronic heart failure including arrhythmia, angina pectoris, myocardial infarction, cardiac insufficiency and congestive heart failure, arteriosclerosis, including atherosclerosis, hypertension, deep vein thrombosis, occlusive peripheral circulation failure, ischemic cerebral circulation failure, disseminated intravascular coagulation syndrome, Raynaud's disease, Buerger disease.

Allergic diseases that may be treated with compounds according to formula I comprise asthma, allergic rhinitis, conjunctivitis, digestive tract allergy, pollinosis and anaphylaxis, chronic occlusive pulmonary disease, collagenosis.

Neurodegenerative diseases that may be treated with compounds according to formula I comprise Alzheimer's disease, Parkinson's disease, amyotrophic lateral sclerosis, AIDS, encephalopathy.

Central nervous failure that may be treated with compounds according to formula I comprise cerebrovascular failure such as cerebral hemorrhage and cerebral infarction and its sequelae, cranial trauma, spinal damage, cerebral edema, dementia, memory failure, consciousness failure, multiple sclerosis.

Toxemia that may be treated with the claimed compounds comprises sepsis, septic shock, endotoxic shock, gram negative sepsis, toxin shock syndrome.

Endocrine disease that may be treated with compounds according to formula I comprises Addison disease, Cushing's syndrome, melanocytoma and primary aldosteronism.

Autoimmune disease that may be treated with compounds according to formula I comprises organ specific diseases such as thyroiditis or non-specific organ diseases such as rheumatoid and osteo-arthritis.

Bone disease that may be treated with compounds according to formula I comprises fracture, re-fracture, osteoporosis, osteomalacia, bone Behcet disease, ankylosing spondylitis, chronic rheumatoid arthritis and osteogonarthritis as well as articular tissue destruction in disease related thereto.

Neurological disorders that may be treated with compounds according to formula I comprise trauma, injury, compression to individual nerves, nerve roots, spinal cord and/or the brain, acute spinal cord and brain injury, demyelinating diseases, such as multiple sclerosis, spinal cord compression due to metastatic cancer, primary or metastatic brain tumors, chronic pain syndromes due to metastatic tumor, inflammatory CNS diseases, such as subacute sclerosing panenencephalitis, Huntington's disease, Guillain-Barre syndrome, Bell's palsy, diabetic neuropathy, optic neuritis, macular degeneration, retinitis pigmentosa, diabetic retinopathy, muscular dystrophy, and polymyositis-dermatomyositis.

Aberrant apoptosis that may be treated with compounds according to formula I comprises any virally-induced inhibition of apoptosis.

Complications of diabetes mellitus or stress hyperglycemia include, for example, any one or more of the following: myocardia infarction, congestive heart failure and cardiogenic shock.

The presence of an adiponectin deficit in an individual can be readily detected in a patient by any means standard in the art, such as by measurement of systemic adiponectin levels by standard ELISA methods. The skilled artisan may be motivated to undertake such testing, for example, based on the nature of the disorder afflicting the patient.

The amount of the disclosed therapeutic compound that will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation also will depend on the route of administration and the seriousness of the disease, disorder, or condition and is decided according to the judgment of the practitioner and each patient's circumstances.

V. ADMINISTRATION OF COMPOUNDS OF FORMULA I

In an embodiment of the invention, the compounds of formula I are administered by way of a continuous-release transdermal patch. However, the compounds may be administered by any route, including oral, rectal, pulmonary, sublingual, and parenteral administration. Parenteral administration includes, for example, intravenous, intramuscular, intraarterial, intravesical (e.g., to the bladder), intradermal, transdermal, topical or subcutaneous administration.

Typically it is contemplated that treatment would be given at least once per day, typically once, twice, three times or four times per day with the doses given at equal intervals throughout the day and night in order to maintain a constant presence of the drug in order to induce sufficient agonistic activity in adiponectin receptor. However, the skilled artisan will be aware that a treatment schedule can be optimized for any given patient, and that administration of compound may occur less frequently than once per day.

One or more compounds of the invention may be administered simultaneously, by the same or different routes, or at different times during treatment. The compounds of the invention may also be prescribed to be taken in combination with other drugs used to treat proliferative disorders. When used in such combinations compounds of the invention and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the compounds no longer produce a beneficial effect. The treating physician will know how to increase, decrease, or interrupt treatment based on patient response.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 5 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Identification of the Active Site of Adiponectin and the Peptide Binding Domain of the AdipoR1

Peptide Design and Synthesis

The full-length amino acid sequence of human adiponectin is set forth in SEQ ID NO: 8.

To test the agonistic (and potentially antagonistic) effects of isolated adiponectin domains, the following adiponectin peptide fragment derivatives were synthesized in a manner in which the C-terminal carboxylic acid function was converted to an amide, —C(O)—NH$_2$. The peptides were synthesized on a β-alanine derivatized cleavable cellulose membrane. Frank R: *J Immunol Methods* 2002, 267(1):13-26. All peptides thus contained an amidated C-terminal β-AlaNH$_2$ residue.

The adiponectin fragment derivatives that were synthesized were:

```
ADP 25-β-AlaNH₂ (amino acids 153-162 of
adiponectin):
                                  (SEQ ID NO: 7)
Asn-Ile-Pro-Gly-Leu-Tyr-Tyr-Phe-Ala-Tyr-β-AlaNH₂

ADP 91-β-AlaNH₂:
                                  (SEQ ID NO: 41)
D-Asn-Ile-Pro-Gly-Leu-Tyr-Tyr-Phe-Ala-D-Ser-β-

AlaNH₂

ADP 157-β-AlaNH₂:
                                  (SEQ ID NO: 42)
Asn-Ile-Pro-Nva-Leu-Tyr-Tyr-Phe-Ala-Tyr-β-AlaNH₂

ADP 223-β-AlaNH₂:
                                  (SEQ ID NO: 43)
Asn-Ile-Pro-Gly-Leu-Tyr-D-Ser-Phe-Ala-Tyr-β-AlaNH₂

ADP 289-β-AlaNH₂:
                                  (SEQ ID NO: 44)
Asn-Ile-Pro-Nva-Leu-Tyr-D-Ser-Phe-Ala-Tyr-β-AlaNH₂

ADP 355-β-AlaNH₂:
                                  (SEQ ID NO: 5)
D-Asn-Ile-Pro-Nva-Leu-Tyr-D-Ser-Phe-Ala-D-Ser-β-

AlaNH₂
```

The ADP25-β-AlaNH$_2$ family of peptides was assembled by Fmoc-synthesis techniques on cellulose sheets, individually cut from the solid support and cleaved from the cellulose membrane by using 2% aqueous triethyl amine overnight. Fields G B, Noble R L. *Int J Pept Protein Res* 1990, 35(3): 161-214. Hilpert K, Winkler D F, Hancock R E: *Nat Protoc* 2007, 2(6):1333-1349. Peptide ADP25-β-AlaNH$_2$ and its modified analogs were purified by reversed-phase high performance liquid chromatography (RP-HPLC) and characterized by matrix-assisted laser desorption/ionization mass spectroscopy (MALDI-MS).

Synthesis and Purification of Individual Peptides.

The active adiponectin peptide ADP 25-NH$_2$, a six-residue middle fragment of it, and peptidomimetic ADP 355-NH$_2$, as well as biotin-labeled analogs of the AdipoR1 extracellular loops, were synthesized on the solid-phase by using a CEM Liberty microwave-assisted peptide synthesizer and utilizing Fmoc-chemistry. Fields G B, Noble R L. *Int J Pept Protein Res* 1990, 35(3):161-214. Biotin was coupled to the peptides while still attached the solid-phase carrier. After cleavage with 95% aqueous trifluoroacetic acid (TFA) containing 2% thioanisole, the peptides were purified by RPHPLC. MALDI-MS verified the high purity of the peptide preparations. After purification, peptide ADP 355-NH$_2$ was lyophilized twice from 2% aqueous acetic acid solution prior to cellular efficacy studies.

Screening of AdipoR1/Peptide Binding.

The unmodified adiponectin array peptides were individually dried down to wells of an ELISA plate, and tested for binding to biotin-labeled linear synthetic models of the 4 extracellular loops of AdipoR1. The receptor/peptide binding was detected by horseradish-peroxidase conjugated streptavidin.

In Vitro Screening of Adiponectin-Based Peptides.

Biological activity of the peptides was first assessed using MCF-7 breast cancer cells that express AdipoR1. Arditi J D, Venihaki M, Karalis K P, Chrousos G P *Horm Metab Res* 2007, 39(1):9-13. The MCF-7 breast cancer cell line was obtained from ATCC (Manassas, Va.) and routinely grown in DMEM:F12 plus 5% calf serum (Cellgro Mediatech, Manassas, Va.) at 37° C., 5% CO$_2$. For screening experiments, MCF-7 cells were plated in 24-well plates at the concentration of 30,000 cells/well. After 12 h of culture in the growth medium, the cells were synchronized in serum-free medium (SFM) (DMEM:F12 supplemented with 0.42 g/mL bovine serum albumin, 1 mM FeSO$_4$ and 2 mM L-glutamine) for 24 h and then shifted back to the full growth medium containing either gAd (Phoenix Secretomics, Burlingame, Calif.) at 50 ng/mL, individual peptides, or no test compounds for 24 h. At conclusion of proliferation assays, the cells were counted under the microscope with trypan-blue exclusion. Each experiment was performed in triplicate and repeated at least three times. ADP 25-β-AlaNH$_2$, ADP 91-β-AlaNH$_2$, ADP 157-β-AlaNH$_2$, ADP 223-β-AlaNH$_2$, ADP 289-β-AlaNH$_2$ and ADP 355-β-AlaNH$_2$ were solubilized at 65° C. for 30 min and were further purified by RP-HPLC and screened together with the individually synthesized adiponectin peptides at the exact concentration of 50 ng/mL.

The peptides were tested for their cytostatic activity in MCF-7 breast cancer cells. In control experiments, globular adiponectin (gAd) was used at 50 ng/mL, a concentration that induced maximal growth inhibition in our dose response experiments in MCF-7 cells (data not shown) and has been described as cytostatic in breast cancer cells. Grossmann M E, et al. *Br J Cancer* 2008, 98(2):370-379. ADP 25-β-AlaNH$_2$ at 50 ng/mL concentration inhibited MCF-7 cell proliferation by 20% relative to untreated controls (FIG. 1A), while other peptides flanking this domain were ineffective or produced only minor cytostatic effects. gAd restricted MCF-7 cell growth by ~18% (FIG. 1A). In parallel experiments, peptides were identified covering the active site displayed the highest affinity to an extended version of the most N-terminal AdipoR1 (loop1, sequence: Arg-Pro-Asn-Met-Tyr-Phe-Met-Ala-Pro-Leu-Gln-Glu-Lys-Val-Val (SEQ ID NO: 60)). No specific binding to other AdipoR1 loops was detected.

Figure 1B:
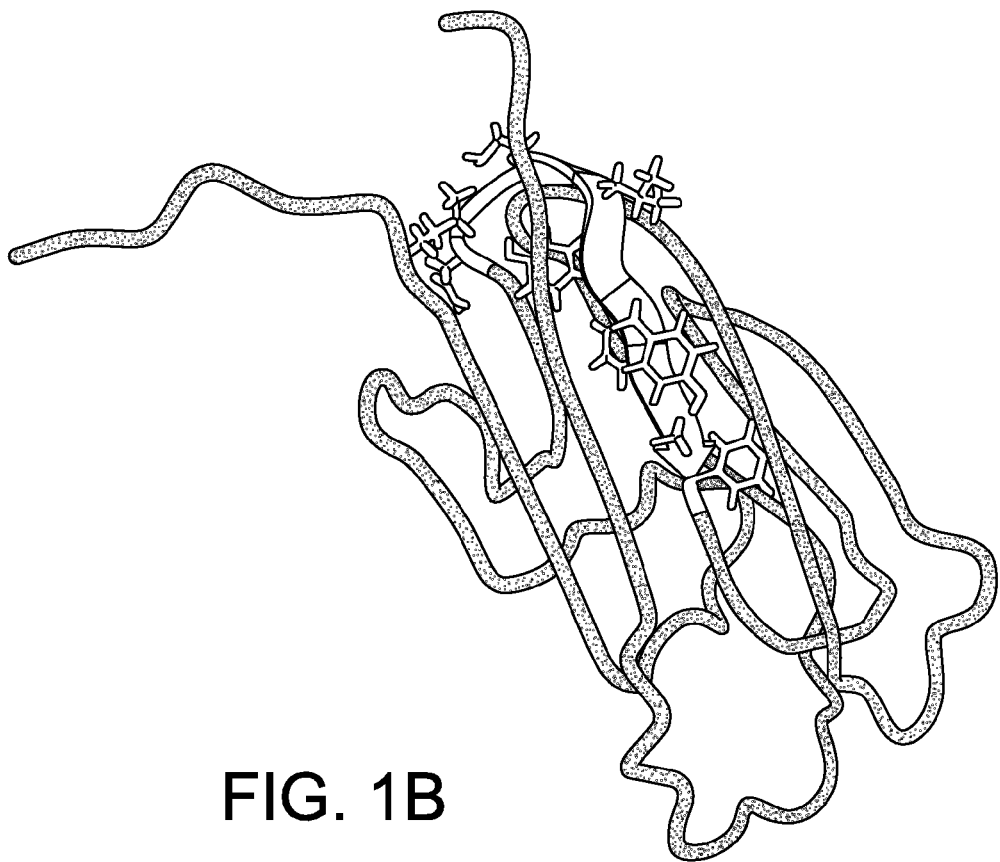
FIG. 1B shows a high-resolution structure of the adiponectin monomer bound to ADP 25-βAlaNH$_2$. Active site amino acid side-chains are depicted in white.

The model of the globular domain of human adiponectin is a β-barrel-type structure in which the β-sheets are connected with ω-loops. The identified active peptide ADP 25-β-AlaNH₂ is located on the loop-β-sheet region of the protein (FIG. 1B). The side-chains of the C-terminal 2/3 of the identified active site are facing outside the adiponectin trimer bundle, which potentially can support interaction with and activation of AdipoR1 (FIG. 1B). The center of the active peptide ADP 25-β-AlaNH₂ has homology only with spastin, immunoglobulin and complement proteins according to a BLAST homology search.

biological activity. Therefore, a 10-residue peptide encompassing ADP 25 was generated and tested. Residues in the 149-166 adiponectin stretch were identified that could be freely replaced with non-natural amino acid analogs and thus empower the drug leads with pharmacological properties that will allow testing the efficacy in animal models, and if successful, forward to clinical development. Table III summarizes the importance of individual residues in biological activity of adiponectin fragments and derivatives. The results allowed identification of a highly active short active site as Ile-Pro-Gly-Leu-Tyr-Tyr-Phe-Ala (SEQ ID NO: 62). Based on structure-function analysis, the conservative substitutions in the minimal active site can be introduced at Gly 155 and Tyr 158 residues without compromising biological activity. Addi-

TABLE III

Summary of structure-function analysis of adiponectin fragment derivative.

| Original Peptide (aa in gAd) | Cytostatic Activity of Original Peptide vs. gAd (% Increase) | Sequence Modifications of Original Peptide | Cytostatic Activity of Modified Peptides vs. gAd (% Increase) |
|---|---|---|---|
| ADP 25-βAla-NH₂ | 11 | Asn-Ile-Pro-Gly-Leu-Tyr-Tyr-Phe-Ala-Tyr<br>  *       *       *       *<br>(SEQ ID NO: 61) | 21-126 |

The cytostatic activity of original and modified peptides or peptidomimetics was evaluated in MCF-7 cells as described supra and is calculated relative to the activity of gAd (baseline). Letters with a * indicate the residues where conservative modifications were made.

Figure 5:
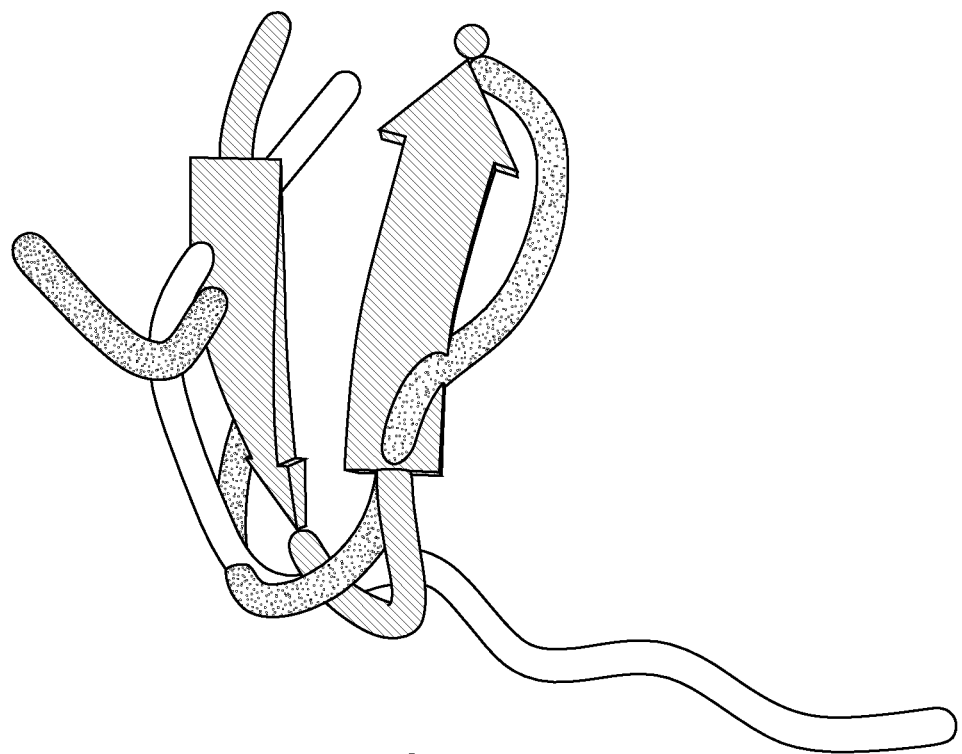
FIG. 5 illustrates ADP 355-NH$_2$ energy analysis. Representative energy minimized structures of ADP 25-NH$_2$ (speckled) and ADP 355-NH$_2$ (hatched arrows) are overlaid to the conformation of the 153-162 sequence found in adiponectin protein (white).

As discussed above, the active site of adiponectin can be characterized as a turn region followed by a β-pleated sheet fragment (FIG. 1B). When removed from the protein environment, Molecular Dynamics (MD) studies indicated that the isolated ADP 25-NH₂ loses the β-pleated sheet character and forms a series of turns (FIG. 5). During MD simulations the initial turn-β-sheet structure of both ADP 25-NH₂ and ADP 355-NH₂ peptides were substantially changed and showed high flexibility. The backbone root mean square deviation (RMSD) values fluctuated with high frequency between 0.1 and 0.7 mm. However, in the case of ADP 355-NH₂, from 80 ns to 250 ns, the RMSD remained around 0.6 nm, indicating that the peptidomimetic folded into a more stable conformation characterized by a hairpin incorporating almost the entire peptide. In the cluster analysis, the most populated cluster of the peptidomimetic contained more than twice as many structures as the native fragment (31.6% vs 12.4%). If the dominant n-hairpin structure is indeed the active conformation, the significantly increased population of this conformer can explain the improved in vitro activity of ADP 355-NH₂ compared to its precursor ADP 25-NH₂.

Identification of Minimal Adiponectin Active Site and Development of its Pharmacologically Improved Analogs.

Next, multiple analogs of ADP 25-β-AlaNH₂ were generated in order to identify the minimal adiponectin active site as well as introduce chemical modifications improving peptide activity and stability. The activities of all ADP 25-β-AlaNH₂ analogs at 50 ng/mL were determined relative to the effects of 50 ng/mL gAd (Table III). While ADP 25-β-AlaNH₂ was fully active in the cancer cell growth inhibition assays, its center 6-residue long fragment 157-162 did not exhibit any biological activity. Therefore, a 10-residue peptide encompassing ADP 25 was generated and tested. Residues in the tions of non-natural amino acids at N- and C-termini are expected to provide stability against exopeptidase cleavage in vitro and in vivo.

Identification of ADP 355-NH₂ as an Optimal Adiponectin Receptor Agonist.

Biological screening of the analogs of adiponectin active site resulted in the identification of a peptidomimetic ADP 355-NH₂ as an optimal AdipoR1 agonist. ADP 355-NH₂ has the sequence DAsn-Ile-Pro-Nva-Leu-Tyr-DSer-Phe-Ala-DSer-NH₂ (SEQ ID NO: 6). The compound is based on the original ADP 25-βAla-NH₂, and contains the minimal active site with allowed modifications (Table III).

Example 2

Synthesis of Alternative Adiponectin Fragment Derivatives

The peptides described in Example 1 were synthesized on a β-alanine derivatized cleavable cellulose membrane. Frank R: *J Immunol Methods* 2002, 267(1):13-26. All peptides thus contained an amidated C-terminal β-AlaNH₂ residue. Alternative adiponectin fragment derivatives may also be made. For example, the β-AlaNH₂ may be cleaved off after peptide synthesis, or the peptide may be synthesized without it to form the following peptides optionally ending with an amide group. For example, "Tyr-NH₂" indicates a tyrosine residue where the carboxylic acid function (—C(O)OH) has been converted to an amide function (—C(O)NH₂):

ADP 25-NH₂ (amino acids 153-162 of adiponectin):
(SEQ ID NO: 45)
Asn-Ile-Pro-Gly-Leu-Tyr-Tyr-Phe-Ala-Tyr-NH₂

ADP 91-NH₂:
(SEQ ID NO: 46)
D-Asn-Ile-Pro-Gly-Leu-Tyr-Tyr-Phe-Ala-D-Ser-NH₂

-continued

ADP 157-NH₂:
(SEQ ID NO: 47)
Asn-Ile-Pro-Nva-Leu-Tyr-Tyr-Phe-Ala-Tyr-NH₂

ADP223-NH₂:
(SEQ ID NO: 48)
Asn-Ile-Pro-Gly-Leu-Tyr-D-Ser-Phe-Ala-Tyr-NH₂

ADP289-NH₂:
(SEQ ID NO: 49)
Asn-Ile-Pro-Nva-Leu-Tyr-D-Ser-Phe-Ala-Tyr-NH₂

ADP355-NH₂:
(SEQ ID NO: 6)
D-Asn-Ile-Pro-Nva-Leu-Tyr-D-Ser-Phe-Ala-D-Ser-NH₂

The corresponding peptides ending with a carboxylic acid function (—C(O)OH) would be:

ADP25 (amino acids 153-162 of adiponectin):
(SEQ ID NO: 50)
Asn-Ile-Pro-Gly-Leu-Tyr-Tyr-Phe-Ala-Tyr ADP91:
(SEQ ID NO: 51)
D-Asn-Ile-Pro-Gly-Leu-Tyr-Tyr-Phe-Ala-D-Ser ADP157:
(SEQ ID NO: 52)
Asn-Ile-Pro-Nva-Leu-Tyr-Tyr-Phe-Ala-Tyr ADP223:
(SEQ ID NO: 53)
Asn-Ile-Pro-Gly-Leu-Tyr-D-Ser-Phe-Ala-Tyr ADP289:
(SEQ ID NO: 54)
Asn-Ile-Pro-Nva-Leu-Tyr-D-Ser-Phe-Ala-Tyr ADP355:
(SEQ ID NO: 3)
D-Asn-Ile-Pro-Nva-Leu-Tyr-D-Ser-Phe-Ala-D-Ser The corresponding peptides ending with an unamidated β-Ala would be:

ADP25-β-Ala (amino acids 153-162 of adiponectin):
(SEQ ID NO: 55)
Asn-Ile-Pro-Gly-Leu-Tyr-Tyr-Phe-Ala-Tyr-β-Ala ADP91-β-Ala:
(SEQ ID NO: 56)
D-Asn-Ile-Pro-Gly-Leu-Tyr-Tyr-Phe-Ala-D-Ser-β-Ala ADP157-β-Ala:
(SEQ ID NO: 57)
Asn-Ile-Pro-Nva-Leu-Tyr-Tyr-Phe-Ala-Tyr-β-Ala ADP223-β-Ala:
(SEQ ID NO: 58)
Asn-Ile-Pro-Gly-Leu-Tyr-D-Ser-Phe-Ala-Tyr-β-Ala ADP289-β-Ala:
(SEQ ID NO: 59)
Asn-Ile-Pro-Nva-Leu-Tyr-D-Ser-Phe-Ala-Tyr-β-Ala ADP355-β-Ala:
(SEQ ID NO: 4)
D-Asn-Ile-Pro-Nva-Leu-Tyr-D-Ser-Phe-Ala-D-Ser-β-Ala Example 3

Breast Cancer Cells Express AdipoR1 and Respond to Adiponectin and ADP 355-NH₂

Using immunohistochemistry (IHC) with specific Abs from Phoenix Pharmaceuticals, AdipoR1 expression was examined in different types of breast cancer. In this preliminary screening, the focus was on triple-negative tumors. In total, 42 cases of triple-negative breast cancer were examined in which AdipoR1 was found in 72%. The receptor was detectable in epithelial, but not stromal, component of tumors (IHC assay and scoring are detailed in Fiorio et al. (2008) *BMC Cancer* 8:305 and Garofalo, C. et al. (2006) *Clin Cancer Res* 12:1447-53). The fact that the receptor can be detected in triple-negative tumors implies that this cancer phenotype will respond to adiponectin agonist treatment at least in more than half of the cases.

Cell Growth Experiments.

The effects of the selected peptide ADP 355-NH₂ on cell proliferation were tested in breast cancer cell lines (MCF-7, MDA-MB-231) and in glioblastoma cells (LN18), all obtained from ATCC and routinely cultured as described previously. Otvos L, Jr., et al. *European J Cancer* 2011, 47(10):1578-1584. Riolfi M, et al. *Brain Pathol* 2010, 20(2): 481-489. Bartucci M, et al. *Cancer Res* 2001, 61(18):6747-6754. The peptide was tested at 10 pM-100 μM concentrations under conditions described above under peptide screening.

Figure 2A:
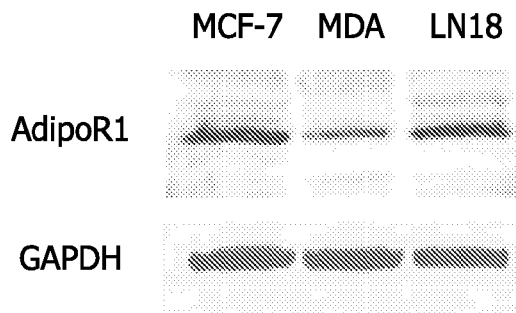
FIG. 2A shows the expression of AdipoR1 in cancer cell lines MCF-7, MDA-MB-231 and LN18 by Western blot, as described in Example 3.

Dose-dependent effects of ADP 355-NH₂ were tested in different cancer cells lines expressing AdipoR1: MCF-7, MDA-MB-231 and LN18. The levels of AdipoR1 were the highest in MCF-7 cells, while the receptor was less abundant in MDA-MB-231 and LN18 cells (FIG. 2A). Preliminary experiments with gAd demonstrated that all cell lines are sensitive to the hormone, and maximal growth inhibition can be achieved with 50-100 ng/mL (data not shown).

Figure 2B:
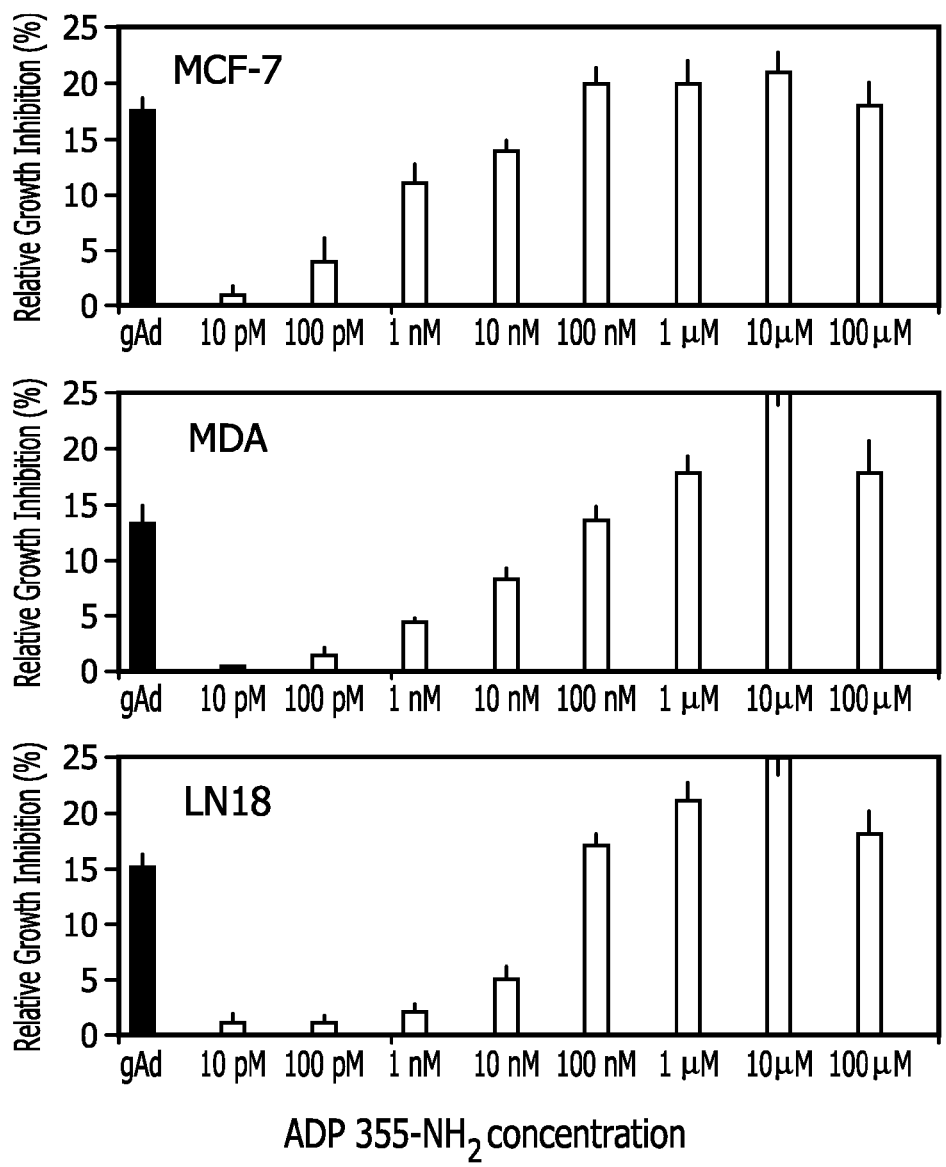
FIG. 2B shows the cytostatic activity of peptide ADP 355-NH$_2$ at 10-100 μM assessed in MCF-7, MDA-MB-231, and LN18 cancer cell lines, as described in Example 3. Bars represent % growth inhibition relative to untreated cells+/−SE.

In all cell lines, ADP 355-NH₂ restricted normal cell growth in a dose-dependent manner. In MCF-7 cells, the best growth inhibition was achieved with a peptide concentration as low as 100 nM and the activity was maintained up to 10 μM. Treatment with 10 pM-10 nM of the peptide was less effective (FIG. 2B).

In MDA-MB-231 and LN 18 cells, similar levels of growth inhibition were achieved at 1 μM with further activity increase at 10 μM. However, a peptide concentration of 100 μM was less inhibitory than a concentration of 1 μM. In all cell lines, ADP 355-NH₂ at maximal effective doses produced greater cytostatic effects than gAd at 50 ng/mL (FIG. 2B).

Figure 6:
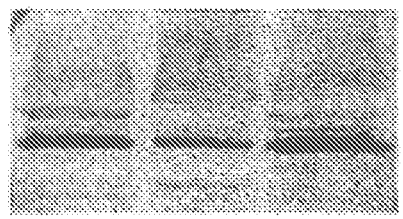
FIG. 6 illustrates expression of AdipoR1 in breast cancer cell lines: MDA-MB-231 (lacking estrogen receptor-α, and progesterone receptor, and expressing negligible levels of HER2), MCF7 (hormone receptor positive, moderately HER2-positive) and ZR751 (hormone receptor positive, moderately HER2-positive). AdipoR1 (approximately 43 kDa) was detected by Western blot in 100 mg of proteins using anti-AdipoR1 antibody (Ab) from Phoenix Pharmaceuticals (in 1:500 dilution).

AdipoR1 appears to play a major role in transmitting antiproliferative adiponectin effects in breast cancer cells. Nakayama, S., Miyoshi, Y., Ishihara, H., Noguchi, S. (2008) *Breast Cancer Res Treat* 112:405-10. The C-terminal adiponectin fragment, the ligand for AdipoR1, inhibits breast cancer cell growth in many models. Grossmann, M E., Nkhata, K J., Mizuno, N K., Ray, A., Cleary, M P. (2008) *Br J Cancer* 98:370-9. Wang, H., Zhang, H., Jia, Z., Zhang, Z., Craig, R., Wang, X., Elbein, S. C. (2004) *Diabetes* 53:2132-6. Because of some discrepancies regarding adiponectin effects and AdipoR1 expression in different cell lines (see Background), AdipoR1 expression was confirmed by Western blot (WB) in cell lines cultured in our laboratory: MDA-MB-231 (lacking estrogen receptor-a, and progesterone receptor, and expressing negligible levels of HER2), MCF7 (hormone receptor positive, moderately HER2-positive) and ZR751 (hormone receptor positive, HER2 positive) (FIG. 6)

Next, it was confirmed that the growth of MCF7 and MDA-MB-231 cells can be consistently inhibited with 50 ng/ml globular adiponectin for 24-72 h. The growth inhibition level in MCF7 and MDA-MB-231 cells was 18-31% and 18-25% respectively [statistically significant (ANOVA, $p<0.05$)]. MCF7, MDA-MB-231 (breast cancer) and LN 18 (glioblastoma) cells were used as our initial cellular models.

Example 4

ADP355-$NH_2$ Differentially Modulates AdipoR Signaling Pathways

Figure 3:
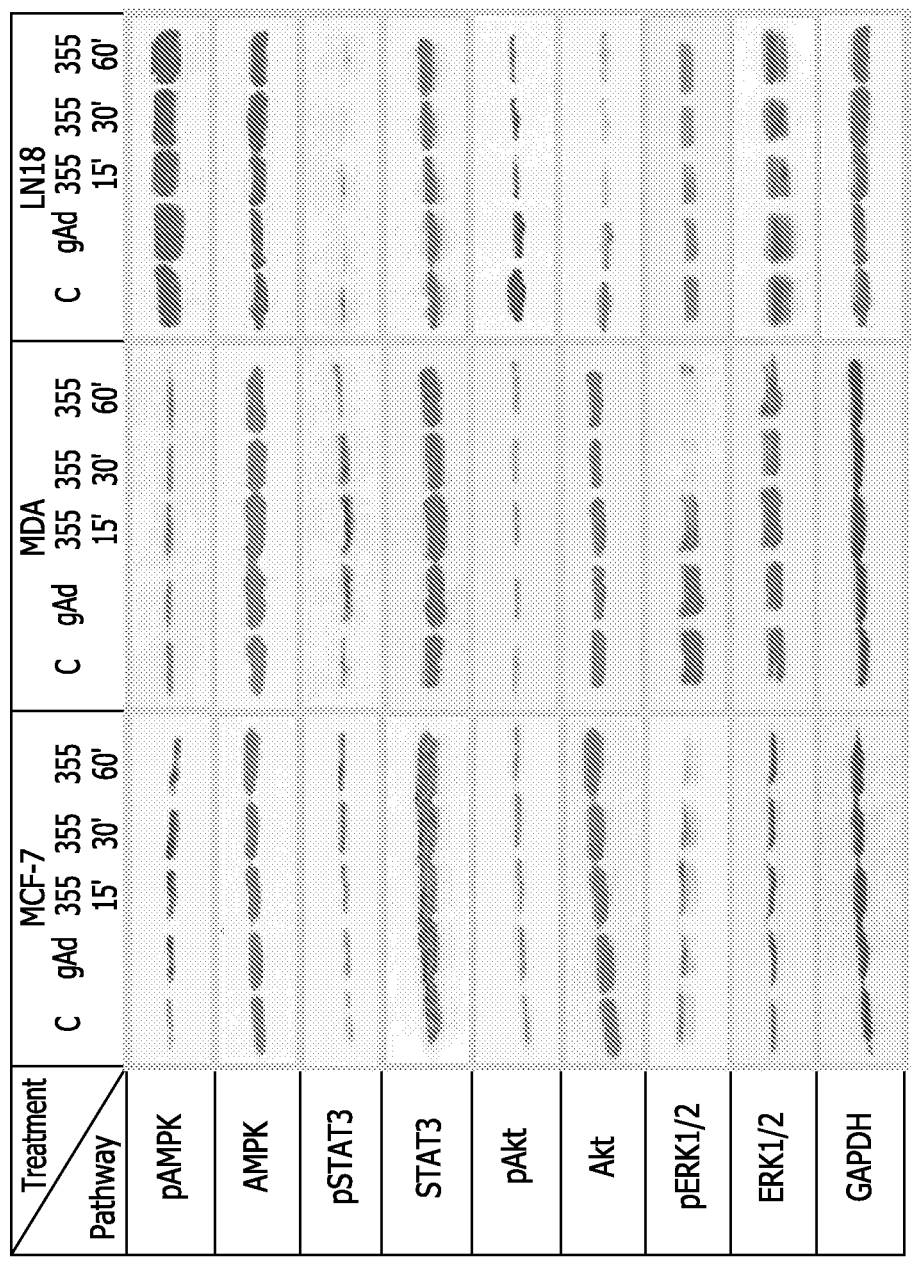
FIG. 3 illustrates the effects of peptide ADP 355-NH$_2$ on intracellular cell signaling in cancer cells. The effects of ADP 355-NH$_2$ on signaling pathways in MCF-7, MDA-MB-231, and LN18 cells at 0-60 minutes of treatment were studied by Western blot, as described in Example 4. The expression of GAPDH was used as determination of protein loading.

The effects of ADP 355-$NH_2$ were examined on different AdipoR1 signaling pathways in MCF-7, MDA-MB-231, and LN18 cells (FIG. 3). The peptide was used at concentrations that exerted maximal cytostatic effects and the treatment was carried out for 0-60 min as detailed below.
Signaling Analysis.

The analysis was done using MCF-7 and MDA-MB-231 breast cancer cells and in LN18 glioblastoma cells. The cells at 70-80% confluence were shifted to SFM for 24 h, then SFM was removed, the cultures were washed 2× with PBS, placed in normal growth medium for 1 h, and then treated with ADP 355-$NH_2$ at 100 nM (MCF-7 cells) or 10 µM (MDA-MB-231 and LN 18 cells) concentration for 0-60 min, while gAd at 50 ng/mL was applied for 60 min only. Untreated cells were used as negative control. After the treatment, cells were lysed as previously described and 100 µg of proteins were analyzed by Western blot for the expression of phosphorylated (p) and total forms of several signaling molecules. Bartella V, et al. *Cancer Res* 2008, 68(12):4919-4927. Garofalo C, et al. *Clin Cancer Res* 2004, 10(10):6466-6475. The following primary antibodies (Abs) from Cell Signaling (Danvers, Mass.) were used: 1) pAMPK alpha (T172) D79.5E rabbit mAb 1: 750; 2) total AMPK alpha antibody rabbit mAb 1:1000 in; 3) p44/42 MAPK (T202/Y204) rabbit mAb 1:1000; 4) total 44/42 MAP kinase antibody rabbit mAb 1:1000; 5) pStat3 (Y705) D3A7 rabbit mAb 1: 500; 6) total Stat3 79D7 rabbit mAb 1:2000; 7) pAkt (Ser 473) rabbit mAb 1:1000; 8) total Akt rabbit mAb 1:1000; 9) AdipoR1 rabbit purified anti-serum 1:500 (Phoenix Secretomics). Protein loading was verified by evaluating the expression of either a constitutive enzyme glyceraldehyde-3-phosphate dehydrogenase (GAPDH) using 6C51 mAbs 1:1000 (Santa Cruz Biotechnology, CA, USA) or alpha-actin using the actin I-19 goat polyclonal Ab (Santa Cruz) 1: 200. The following secondary Abs (Santa Cruz) were used 1) donkey anti-goat IgG-HRP; 2) goat anti-mouse IgG-HRP; 3) goat anti-rabbit IgG-HRP, all applied at 1:1000 dilution.

Remarkably, ADP 355-$NH_2$ exerted differential effects on several signaling pathway depending on cell line. In MCF-7 cells, the peptide increased the phosphorylation of AMPK at 15 and 30 min and decreased ERK1/2 phosphorylation at 60 min. ADP 355-$NH_2$ did not affect the activation of Akt in these cells, but it increased the phosphorylation of STAT3 at 15-60 min (FIG. 3).

In MDA-MB-231 cells, the major pathway affected by ADP 355-$NH_2$, was ERK1/2, which was significantly inhibited at 30 and 60 min of treatment. The peptide transiently increased STAT3 phosphorylation at 15 and 30 min. In MDA-MB-231 cells, ADP 355-$NH_2$ did not affect AMPK or Akt activation. In LN18 cells, ADP 355-$NH_2$ decreased STAT3 phosphorylation at 15-60 min and down-regulated total and phosphorylated levels of Akt at 15-60 min. However, the peptide did not modulate AMPK in these cells. Interestingly, the effects on Akt predominantly concerned total levels of the enzyme, suggesting that ADP 355-$NH_2$ might affect its degradation process. In all cell lines, gAd modulated signaling pathways similar to ADP 355-$NH_2$, however its effects were usually less pronounced (FIG. 3).

These results suggest that growth inhibition by gAd or ADP 355-$NH_2$ can be associated with modulation of different signaling pathways in different cell lines.

Example 5

ADP355-$NH_2$ Exhibits Superior Stability in Mouse Serum and Blood, and is not Toxic In Vivo Peptide Stability in Mouse Blood and Mouse Serum.
Sixty µg of ADP 355-$NH_2$ were dissolved in 100 µL water, and 10 µL aliquots were mixed with 100 µL of freshly drawn mouse blood. After 30 min of incubation at 37° C. the cells were centrifuged at 10,000×g. Fifty µL serum was mixed with 50 µL phosphate buffered saline pH 6.8 (PBS), and the serum proteins were precipitated by addition of 45 µL aqueous 15% trichloroacetic acid (TCA) for 10 min at 4° C. After centrifugation at 12,000×g the supernatant was neutralized with 0.1 M aqueous sodium hydroxide and 0.5 µL of this solution was mixed with 0.5 µL α-cyano-4-hydroxycinnamic acid (4 mg/mL in 60% aqueous acetonitrile containing 0.1% TFA) as matrix on a sample plate. Analysis was performed on a MALDI time-of-flight tandem mass spectrometer (MALDITOF/TOF-MS, 4700 proteomic analyzer, Applied Biosystems, Weiterstadt, Germany). Additionally, the neutralized supernatant was loaded on a Jupiter C18 RP-HPLC column (4.6 mm internal diameter, 150 mm length, 5 µm particle size, 30 nm pore size; Phenomenex) that had previously been calibrated with known amounts of peptide ADP 355-$NH_2$ dissolved in PBS. Absorbance was measured at 214 nm. Peptide ADP 355-$NH_2$ was incubated at 37° C. with 25% aqueous mouse serum at a final concentration of 150 µg/mL. After 0, 15, 30, 60, 120, and 240 min 95 µL aliquots were mixed with 25 µL 15% aqueous TCA and were incubated for 10 min at 4° C. Sample analysis followed the protocols described above.

Figure 4:
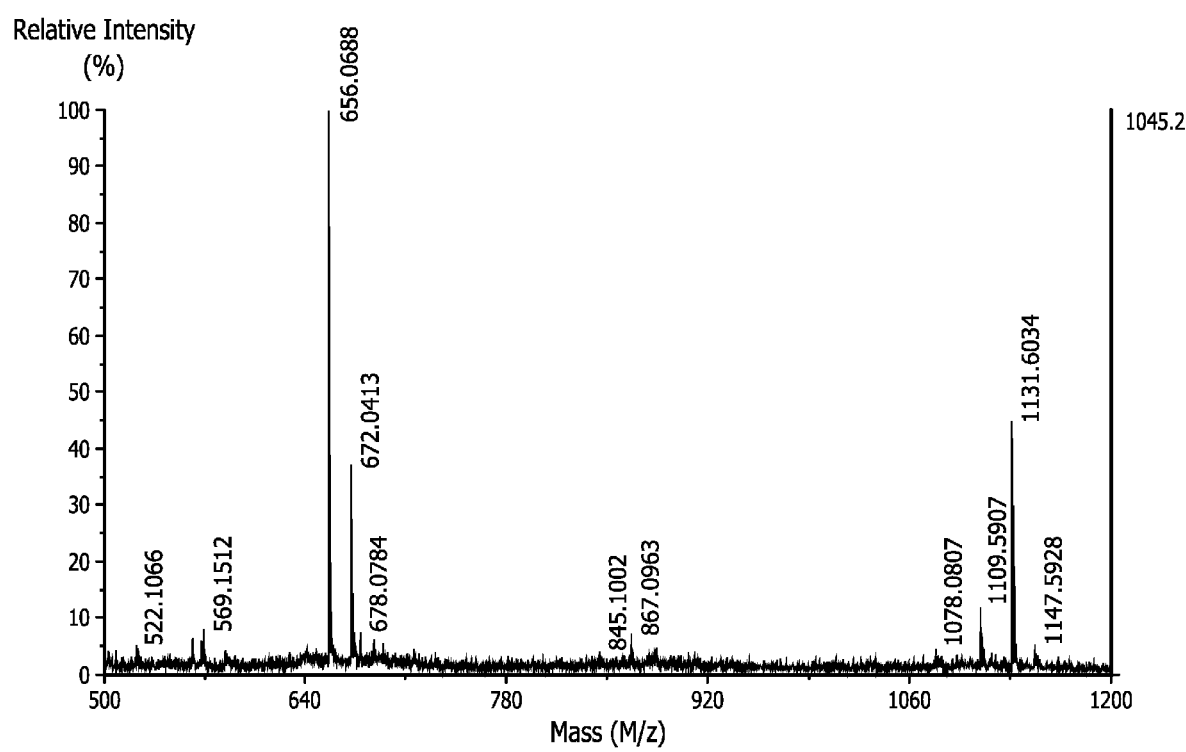
FIG. 4 illustrates the stability of peptide ADP 355-NH$_2$ in whole mouse blood. The peptide stability was assessed in whole mouse blood after 30 minutes of incubation by mass spectroscopy as described in Example 5. The only peptide-originated peaks are at 1109 and 1131 M/z, representing the unmodified peptide and its sodium adduct.

Calculating from the degradation rate measured in 25% aqueous serum, ADP 355-$NH_2$ had a 75 min half-life in mouse serum (data not shown) based on the teachings of Powell M F, et al. *J Pharm Sci* 1992, 81(8):731-735. In whole mouse blood, ADP 355-$NH_2$ was present even after 30 min without noticeable degradation (FIG. 4).
In Vivo Toxicity.

Peptide ADP 355-$NH_2$ was injected into 10-12 week old female CBA/J mice. Bolus intraperitoneal (ip) doses were administered at 5 mg/kg, 10 mg/kg, 25 mg/kg or 50 mg/kg in sterile saline and the animals were observed for signs of systemic toxicity (tremor, head tilt, reduced activity and squinting) for 4 days. On day 5 the mice were killed by $CO_2$ inhalation and the potential peptide elimination organs, the livers, spleens and kidneys were removed and weighed.

Healthy mice receiving up to 50 mg/kg peptide ADP 355-$NH_2$ ip showed no signs of systemic toxicity. Four days after peptide administration the potential peptide elimination organs were removed and weighed. While the spleens of treated animals were identical in size with those of untreated, control mice, the kidney and liver sizes were slightly increased relative to total body weight by 2 and 8%, respectively (Table IV). The minimal increase of liver size could be related to the fact that this organ contains AdipoR1/2 and, as a physiological target of adiponectin, responds to the hormone analog. Kadowaki T, et al. *FEBS Lett* 2008, 582(1):74-80.

TABLE IV

Toxicity analysis of ADP 355-NH$_2$

| Peptide dose (bolus ip) | Liver weight (g); relative to total weight (%) | Spleen weight (g) | Kidney weight (g); relative to total weight (%) |
|---|---|---|---|
| Untreated | 0.98; 0.054 | 0.07 | 0.29; 0.015 |
| 5 mg/kg | 1.02; 0.054 | 0.07 | 0.30; 0.016 |
| 10 mg/kg | 1.09; 0.059 | 0.06 | 0.29; 0.016 |
| 25 mg/kg | 1.24; 0.059 | 0.07 | 0.35; 0.017 |
| 50 mg/kg | 1.07; 0.062 | 0.07 | 0.31; 0.017 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula I:

X-M1-SEQ ID NO:1-M2-Z    (I)

wherein SEQ ID NO:1 is Xaa1-Ile-Pro-Xaa2-Leu-Tyr-Xaa3-Phe-Ala-Xaa4-Xaa5, wherein:
(a) Xaa1 is Asn or a non-natural amino acid;
(b) Xaa2 is Gly or a non-natural amino acid;
(c) Xaa3 is Tyr or a non-natural amino acid;
(d) Xaa4 is Tyr or a non-natural amino acid;
(e) Xaa5 is no amino acid, β-Ala or β-AlaNH$_2$;
provided, at least one of Xaa1, Xaa2, Xaa3, or Xaa4 is a non-natural amino acid;
X is an optionally present
 1-10 amino acid peptide,
 linear or branched polyethylene glycol having a molecular weight of from 1 kDa to 200 kDa,
 lipophilic compound or
 peptide transduction domain;
Z is an optionally present
 1-10 amino acid peptide,
 linear or branched polyethylene glycol having a molecular weight of from 1 kDa to 200 kDa,
 lipophilic compound or
 peptide transduction domain;
M1 is an optionally present single bond or a linking group; and
M2 is an optionally present single bond or a linking group;
wherein, when the compound of formula I comprises a C-terminal amino acid, said C-terminal amino acid is optionally amidated;
or a salt thereof.

2. The compound of claim 1, or a salt thereof, wherein
(a) Xaa1 is D-Asn; and
(b) Xaa4 is D-Ser.

3. The compound of claim 1, or a salt thereof, wherein Xaa2 is Nva.

4. The compound of claim 1, or a salt thereof, wherein Xaa3 is D-Ser.

5. The compound of claim 1, or a salt thereof, wherein
(a) Xaa2 is Nva; and
(b) Xaa3 is D-Ser.

6. The compound of claim 1, or a salt thereof, wherein
(a) Xaa1 is D-Asn;
(b) Xaa2 is Nva;
(c) Xaa3 is D-Ser; and
(d) Xaa4 is D-Ser.

7. The compound of any one of claims 1-6, or a salt thereof, wherein Xaa5 is β-Ala or β-AlaNH$_2$.

8. The compound of any one of claims 1-6, according to Formula II:

(II)
(SEQ ID NO: 2)
Xaa1-Ile-Pro-Xaa2-Leu-Tyr-Xaa3-Phe-Ala-Xaa4 wherein the C-terminal amino acid is optionally amidated, or a salt thereof.

9. The compound of claim 1, or a salt thereof, wherein said compound is selected from a group consisting of (SEQ ID NO: 3)
D-Asn-Ile-Pro-Nva-Leu-Tyr-D-Ser-Phe-Ala-D-Ser;

(SEQ ID NO: 4)
D-Asn-Ile-Pro-Nva-Leu-Tyr-D-Ser-Phe-Ala-D-Ser-β-Ala;

(SEQ ID NO: 5)
D-Asn-Ile-Pro-Nva-Leu-Tyr-D-Ser-Phe-Ala-D-Ser-β-AlaNH$_2$;
and (SEQ ID NO: 6)
D-Asn-Ile-Pro-Nva-Leu-Tyr-D-Ser-Phe-Ala-D-Ser-NH$_2$;

or a salt thereof.

10. A method of treating an individual suffering from a cellular proliferative disorder, comprising administering to the individual an effective amount of at least one compound according to claim 1, or a pharmaceutically acceptable salt thereof, wherein the cellular proliferative disorder is selected from the group consisting of hemangiomatosis in newborn, secondary progressive multiple sclerosis, atherosclerosis, chronic progressive myelodegenerative disease, neurofibromatosis, ganglioneuromatosis, keloid formation, Paget's disease of the bone, fibrocystic disease of the breast, uterine fibroids, Peyronie's disease, Dupuytren's disease, restenosis, benign proliferative breast disease, benign prostatic hyperplasia, X linked lymphocellular proliferative disorder, post transplantation lymphocellular proliferative disorder, macular degeneration, retinopathies, proliferative vitreoretinopathy and non-cancerous lymphocellular proliferative disorders.

11. A method of treating an individual suffering from a cancer, wherein the cancer is selected from the group consisting of breast cancer, prostate cancer, colorectal cancer, brain cancer, endometrial cancer, liver cancer, stomach cancer and leukemia, comprising administering to the individual an effective amount of at least one compound according to claim 1, or a pharmaceutically acceptable salt thereof.

12. The method of claim 11 wherein said leukemia is selected from the group consisting of acute myeloid leukemia, chronic myeloid leukemia, acute lymphoid leukemia and chronic lymphoid leukemia.

13. The method according to claim 11 wherein the cancer is selected from the group consisting of breast cancer and glioblastoma.

* * * * *

UNITED STATES PATENT AND TRADEMARK OFFICE
CERTIFICATE OF CORRECTION

| | | |
|---|---|---|
| PATENT NO. | : 9,073,965 B2 | Page 1 of 1 |
| APPLICATION NO. | : 14/110813 | |
| DATED | : July 7, 2015 | |
| INVENTOR(S) | : Laszlo Otvos and Eva Surmacz | |

It is certified that error appears in the above-identified patent and that said Letters Patent is hereby corrected as shown below:

In the Specification

In Column 1, under the "Reference to Government Grant", please replace the text on Lines 14-18 with the following:
-- This invention was made with government support under W81XWH-09-1-0332 awarded by the Medical Research and Development Command and RR016469 awarded by the National Institutes of Health. The government has certain rights in the invention. --

Signed and Sealed this
Twenty-first Day of November, 2023

Katherine Kelly Vidal
*Director of the United States Patent and Trademark Office*

SEQUENCE LISTING

```
<160> NUMBER OF SEQ ID NOS: 62

<210> SEQ ID NO 1
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 may be Asn or a non-natural
      amino acid
<220> FEATURE:
<221> NAME/KEY: MISC_FEATURE
<222> LOCATION: (1)..(11)
<223> OTHER INFORMATION: provided that at least one of positions 1, 4, 7
      or 10 is a non-natural amino acid
<220> FEATURE:
<221> NAME/KEY: MISC_FEATURE
<222> LOCATION: (4)..(4)
<223> OTHER INFORMATION: Xaa at position 4 may be Gly or a non-natural
      amino acid
<220> FEATURE:
<221> NAME/KEY: MISC_FEATURE
<222> LOCATION: (7)..(7)
<223> OTHER INFORMATION: Xaa at position 7 may be Tyr or a non-natural
      amino acid
<220> FEATURE:
<221> NAME/KEY: MISC_FEATURE
<222> LOCATION: (10)..(11)
<223> OTHER INFORMATION: when Xaa at position 10 or Xaa at position 11
      is a C-terminal amino acid, said C-terminal amino acid is
      optionally amidated
<220> FEATURE:
<221> NAME/KEY: MISC_FEATURE
<222> LOCATION: (10)..(10)
<223> OTHER INFORMATION: Xaa at position 10 may be Tyr or a non-natural
      amino acid
<220> FEATURE:
<221> NAME/KEY: MISC_FEATURE
<222> LOCATION: (11)..(11)
<223> OTHER INFORMATION: Xaa at position 11 may be absent, bAla or
      bAlaNH2

<400> SEQUENCE: 1

Xaa Ile Pro Xaa Leu Tyr Xaa Phe Ala Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is Asn or a non-natural amino
```

```
                       acid
<220> FEATURE:
<221> NAME/KEY: MISC_FEATURE
<222> LOCATION: (1)..(10)
<223> OTHER INFORMATION: provided that at least one of Xaa at position
      1, Xaa at position 4, Xaa at position 7 or Xaa at position 10 is a
      non-natural amino acid
<220> FEATURE:
<221> NAME/KEY: MISC_FEATURE
<222> LOCATION: (1)..(10)
<223> OTHER INFORMATION: wherein the C-terminal amino acid is optionally
      amidated
<220> FEATURE:
<221> NAME/KEY: MISC_FEATURE
<222> LOCATION: (4)..(4)
<223> OTHER INFORMATION: Xaa at position 4 is Gly or a non-natural amino
      acid
<220> FEATURE:
<221> NAME/KEY: MISC_FEATURE
<222> LOCATION: (7)..(7)
<223> OTHER INFORMATION: Xaa at position 7 is Tyr or a non-natural amino
      acid
<220> FEATURE:
<221> NAME/KEY: MISC_FEATURE
<222> LOCATION: (10)..(10)
<223> OTHER INFORMATION: Xaa at position 10 is Tyr or a non-natural
      amino acid

<400> SEQUENCE: 2

Xaa Ile Pro Xaa Leu Tyr Xaa Phe Ala Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser

<400> SEQUENCE: 3

Xaa Ile Pro Xaa Leu Tyr Xaa Phe Ala Xaa
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
```

```
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser
<220> FEATURE:
<221> NAME/KEY: MISC_FEATURE
<222> LOCATION: (11)..(11)
<223> OTHER INFORMATION: Xaa at position 11 is bAla

<400> SEQUENCE: 4

Xaa Ile Pro Xaa Leu Tyr Xaa Phe Ala Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser
<220> FEATURE:
<221> NAME/KEY: MISC_FEATURE
<222> LOCATION: (11)..(11)
<223> OTHER INFORMATION: Xaa at position 11 is bAlaNH2

<400> SEQUENCE: 5

Xaa Ile Pro Xaa Leu Tyr Xaa Phe Ala Xaa Xaa
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is D-Ser-NH2

<400> SEQUENCE: 6

Xaa Ile Pro Xaa Leu Tyr Xaa Phe Ala Xaa
1               5                   10
```

```
<210> SEQ ID NO 7
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa at position 11 is bAlaNH2

<400> SEQUENCE: 7

Asn Ile Pro Gly Leu Tyr Tyr Phe Ala Tyr Xaa
1               5                   10

<210> SEQ ID NO 8
<211> LENGTH: 244
<212> TYPE: PRT
<213> ORGANISM: Homo sapiens

<400> SEQUENCE: 8

Met Leu Leu Leu Gly Ala Val Leu Leu Leu Ala Leu Pro Gly His
1               5                   10                  15

Asp Gln Glu Thr Thr Thr Gln Gly Pro Gly Val Leu Leu Pro Leu Pro
                20                  25                  30

Lys Gly Ala Cys Thr Gly Trp Met Ala Gly Ile Pro Gly His Pro Gly
            35                  40                  45

His Asn Gly Ala Pro Gly Arg Asp Gly Arg Asp Gly Thr Pro Gly Glu
        50                  55                  60

Lys Gly Glu Lys Gly Asp Pro Gly Leu Ile Gly Pro Lys Gly Asp Ile
65                  70                  75                  80

Gly Glu Thr Gly Val Pro Gly Ala Glu Gly Pro Arg Gly Phe Pro Gly
                85                  90                  95

Ile Gln Gly Arg Lys Gly Glu Pro Gly Glu Gly Ala Tyr Val Tyr Arg
            100                 105                 110

Ser Ala Phe Ser Val Gly Leu Glu Thr Tyr Val Thr Ile Pro Asn Met
        115                 120                 125

Pro Ile Arg Phe Thr Lys Ile Phe Tyr Asn Gln Gln Asn His Tyr Asp
    130                 135                 140

Gly Ser Thr Gly Lys Phe His Cys Asn Ile Pro Gly Leu Tyr Tyr Phe
145                 150                 155                 160

Ala Tyr His Ile Thr Val Tyr Met Lys Asp Val Lys Val Ser Leu Phe
                165                 170                 175

Lys Lys Asp Lys Ala Met Leu Phe Thr Tyr Asp Gln Tyr Gln Glu Asn
            180                 185                 190

Asn Val Asp Gln Ala Ser Gly Ser Val Leu Leu His Leu Glu Val Gly
        195                 200                 205

Asp Gln Val Trp Leu Gln Val Tyr Gly Glu Gly Glu Arg Asn Gly Leu
    210                 215                 220

Tyr Ala Asp Asn Asp Asn Asp Ser Thr Phe Thr Gly Phe Leu Leu Tyr
225                 230                 235                 240

His Asp Thr Asn

<210> SEQ ID NO 9
<211> LENGTH: 137
<212> TYPE: PRT
<213> ORGANISM: Homo sapiens

<400> SEQUENCE: 9
```

```
Ala Tyr Val Tyr Arg Ser Ala Phe Ser Val Gly Leu Glu Thr Tyr Val
1               5                   10                  15

Thr Ile Pro Asn Met Pro Ile Arg Phe Thr Lys Ile Pro Tyr Asn Gln
            20                  25                  30

Gln Asn His Tyr Asp Gly Ser Thr Gly Lys Phe His Cys Asn Ile Pro
            35                  40                  45

Gly Leu Tyr Tyr Phe Ala Tyr His Ile Thr Val Tyr Met Lys Asp Val
        50                  55                  60

Lys Val Ser Leu Phe Lys Asp Lys Ala Met Leu Phe Thr Tyr Asp
65                  70                  75                  80

Gln Tyr Gln Glu Asn Asn Val Asp Gln Ala Ser Gly Ser Val Leu Leu
            85                  90                  95

His Leu Glu Val Gly Asp Gln Val Trp Leu Gln Val Tyr Gly Glu Gly
            100                 105                 110

Glu Arg Asn Gly Leu Tyr Ala Asp Asn Asp Asn Asp Ser Thr Phe Thr
            115                 120                 125

Gly Phe Leu Leu Tyr His Asp Thr Asn
            130                 135
```

```
<210> SEQ ID NO 10
<211> LENGTH: 12
<212> TYPE: PRT
<213> ORGANISM: Human immunodeficiency virus

<400> SEQUENCE: 10

Tyr Gly Arg Lys Lys Arg Arg Gln Arg Arg Gly
1               5                   10

<210> SEQ ID NO 11
<211> LENGTH: 14
<212> TYPE: PRT
<213> ORGANISM: Human immunodeficiency virus

<400> SEQUENCE: 11

Gly Arg Lys Lys Arg Arg Gln Arg Arg Pro Pro Gln Cys
1               5                   10

<210> SEQ ID NO 12
<211> LENGTH: 13
<212> TYPE: PRT
<213> ORGANISM: Human immunodeficiency virus

<400> SEQUENCE: 12

Gly Arg Lys Lys Arg Arg Gln Arg Arg Arg Pro Pro Gln
1               5                   10

<210> SEQ ID NO 13
<211> LENGTH: 11
<212> TYPE: PRT
<213> ORGANISM: Human immunodeficiency virus

<400> SEQUENCE: 13

Tyr Gly Arg Lys Lys Arg Arg Gln Arg Arg Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Chemically synthesized
```

```
<400> SEQUENCE: 14

Tyr Ala Arg Lys Ala Arg Arg Gln Ala Arg Arg
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Chemically synthesized

<400> SEQUENCE: 15

Tyr Ala Arg Ala Ala Ala Arg Gln Ala Arg Ala
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Chemically synthesized

<400> SEQUENCE: 16

Tyr Ala Arg Ala Ala Arg Arg Ala Ala Arg Arg
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Chemically synthesized

<400> SEQUENCE: 17

Tyr Ala Arg Ala Ala Arg Arg Ala Ala Arg Ala
1               5                   10

<210> SEQ ID NO 18
<211> LENGTH: 16
<212> TYPE: PRT
<213> ORGANISM: Artificial Sequence
<220> FEATURE:
<223> OTHER INFORMATION: Chemically synthesized

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Chemically synthesized

<400> SEQUENCE: 19

Lys Lys Trp Lys Met Arg Arg Asn Gln Phe Trp Val Lys Val Gln Arg
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Chemically synthesized

<400> SEQUENCE: 20
```

```
Arg Arg Trp Arg Arg Trp Trp Arg Arg Trp Trp Arg Trp Arg Arg
1               5                   10                  15

<210> SEQ ID NO 21
<211> LENGTH: 7
<212> TYPE: PRT
<213> ORGANISM: Artificial Sequence
<220> FEATURE:
<223> OTHER INFORMATION: Chemically synthesized

<400> SEQUENCE: 21

Arg Arg Met Lys Trp Lys Lys
1               5

<210> SEQ ID NO 22
<211> LENGTH: 7
<212> TYPE: PRT
<213> ORGANISM: Artificial Sequence
<220> FEATURE:
<223> OTHER INFORMATION: Chemically synthesized

<400> SEQUENCE: 22

Arg Arg Arg Arg Arg Arg Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Chemically synthesized

<400> SEQUENCE: 23

Arg Arg Arg Arg Arg Arg Arg Arg Arg
1               5

<210> SEQ ID NO 24
<211> LENGTH: 30
<212> TYPE: PRT
<213> ORGANISM: Artificial Sequence
<220> FEATURE:
<223> OTHER INFORMATION: Chemically synthesized

<400> SEQUENCE: 24

Asn Ala Ala Thr Arg Ser Ala Ala Ser Arg Pro Thr Gln Arg Pro Arg
1               5                   10                  15

Ala Pro Ala Arg Ser Ala Ser Arg Pro Arg Arg Pro Val Glu
            20                  25                  30

<210> SEQ ID NO 25
<211> LENGTH: 16
<212> TYPE: PRT
<213> ORGANISM: Artificial Sequence
<220> FEATURE:
<223> OTHER INFORMATION: Chemically synthesized

<400> SEQUENCE: 25

Gly Ala Leu Phe Leu Gly Trp Leu Gly Ala Ala Gly Ser Thr Met Gly
1               5                   10                  15

<210> SEQ ID NO 26
<211> LENGTH: 27
<212> TYPE: PRT
<213> ORGANISM: Artificial Sequence
<220> FEATURE:
<223> OTHER INFORMATION: Chemically synthesized
```

```
<400> SEQUENCE: 26

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 27
<211> LENGTH: 27
<212> TYPE: PRT
<213> ORGANISM: Caiman crocodilus

<400> SEQUENCE: 27

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

<210> SEQ ID NO 28
<211> LENGTH: 12
<212> TYPE: PRT
<213> ORGANISM: Hepatitis B virus

<400> SEQUENCE: 28

Pro Leu Ser Ser Ile Phe Ser Arg Ile Gly Asp Pro
1               5                   10

<210> SEQ ID NO 29
<211> LENGTH: 12
<212> TYPE: PRT
<213> ORGANISM: Hepatitis A virus

<400> SEQUENCE: 29

Phe Trp Arg Gly Asp Leu Val Phe Asp Phe Gln Val
1               5                   10

<210> SEQ ID NO 30
<211> LENGTH: 25
<212> TYPE: PRT
<213> ORGANISM: Vesicular stomatitis virus

<400> SEQUENCE: 30

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 31
<211> LENGTH: 20
<212> TYPE: PRT
<213> ORGANISM: Artificial Sequence
<220> FEATURE:
<223> OTHER INFORMATION: Chemically synthesized

<400> SEQUENCE: 31

Ala Lys Arg Ala Arg Leu Ser Thr Ser Phe Asn Pro Val Tyr Pro Tyr
1               5                   10                  15

Glu Asp Glu Ser
            20

<210> SEQ ID NO 32
<211> LENGTH: 27
<212> TYPE: PRT
```

```
<213> ORGANISM: Artificial Sequence
<220> FEATURE:
<223> OTHER INFORMATION: Chemically synthesized

<400> SEQUENCE: 32

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 33
<211> LENGTH: 18
<212> TYPE: PRT
<213> ORGANISM: Artificial Sequence
<220> FEATURE:
<223> OTHER INFORMATION: Chemically synthesized

<400> SEQUENCE: 33

Arg Gly Gly Arg Leu Ser Tyr Ser Arg Arg Arg Phe Ser Thr Ser Thr
1               5                   10                  15

Gly Arg

<210> SEQ ID NO 34
<211> LENGTH: 16
<212> TYPE: PRT
<213> ORGANISM: Kaposi's sarcoma-associated herpesvirus

<400> SEQUENCE: 34

Ala Ala Val Ala Leu Leu Pro Ala Val Leu Leu Ala Leu Leu Ala Pro
1               5                   10                  15

<210> SEQ ID NO 35
<211> LENGTH: 12
<212> TYPE: PRT
<213> ORGANISM: Kaposi's sarcoma-associated herpesvirus

<400> SEQUENCE: 35

Ala Ala Val Leu Leu Pro Val Leu Leu Ala Ala Pro
1               5                   10

<210> SEQ ID NO 36
<211> LENGTH: 15
<212> TYPE: PRT
<213> ORGANISM: Homo sapiens

<400> SEQUENCE: 36

Val Thr Val Leu Ala Leu Gly Ala Leu Ala Gly Val Gly Val Gly
1               5                   10                  15

<210> SEQ ID NO 37
<211> LENGTH: 30
<212> TYPE: PRT
<213> ORGANISM: Artificial Sequence
<220> FEATURE:
<223> OTHER INFORMATION: Chemically synthesized

<400> SEQUENCE: 37

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 38
<211> LENGTH: 18
```

```
<212> TYPE: PRT
<213> ORGANISM: Artificial Sequence
<220> FEATURE:
<223> OTHER INFORMATION: Chemically synthesized

<400> SEQUENCE: 38

Lys Leu Ala Leu Lys Leu Ala Leu Lys Ala Leu Lys Ala Ala Leu Lys
1               5                   10                  15

Leu Ala

<210> SEQ ID NO 39
<211> LENGTH: 30
<212> TYPE: PRT
<213> ORGANISM: Artificial Sequence
<220> FEATURE:
<223> OTHER INFORMATION: Chemically synthesized

<400> SEQUENCE: 39

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 40
<211> LENGTH: 12
<212> TYPE: PRT
<213> ORGANISM: Artificial Sequence
<220> FEATURE:
<223> OTHER INFORMATION: Chemically synthesized

<400> SEQUENCE: 40

Arg Arg Gln Arg Arg Thr Ser Lys Leu Met Lys Arg
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (10)..(10)
<223> OTHER INFORMATION: Xaa at position 10 is D-Ser
<220> FEATURE:
<221> NAME/KEY: MISC_FEATURE
<222> LOCATION: (11)..(11)
<223> OTHER INFORMATION: Xaa at position 11 is bAlaNH2

<400> SEQUENCE: 41

Xaa Ile Pro Gly Leu Tyr Tyr Phe Ala Xaa Xaa
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
```

<222> LOCATION: (11)..(11)
<223> OTHER INFORMATION: Xaa at position 11 is bAlaNH2

<400> SEQUENCE: 42

Asn Ile Pro Xaa Leu Tyr Tyr Phe Ala Tyr Xaa
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (11)..(11)
<223> OTHER INFORMATION: Xaa at position 11 is bAlaNH2

<400> SEQUENCE: 43

Asn Ile Pro Gly Leu Tyr Xaa Phe Ala Tyr Xaa
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (11)..(11)
<223> OTHER INFORMATION: Xaa at position 11 is bAlaNH2

<400> SEQUENCE: 44

Asn Ile Pro Xaa Leu Tyr Xaa Phe Ala Tyr Xaa
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (10)..(10)
<223> OTHER INFORMATION: Xaa at position 10 is Tyr-NH2

<400> SEQUENCE: 45

Asn Ile Pro Gly Leu Tyr Tyr Phe Ala Xaa
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Chemically synthesized
<220> FEATURE:

```
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (10)..(10)
<223> OTHER INFORMATION: Xaa at position 10 is D-Ser-NH2

<400> SEQUENCE: 46

Xaa Ile Pro Gly Leu Tyr Tyr Phe Ala Xaa
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (10)..(10)
<223> OTHER INFORMATION: Xaa at position 10 is Tyr-NH2

<400> SEQUENCE: 47

Asn Ile Pro Xaa Leu Tyr Tyr Phe Ala Xaa
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is Tyr-NH2

<400> SEQUENCE: 48

Asn Ile Pro Gly Leu Tyr Xaa Phe Ala Xaa
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (10)..(10)
<223> OTHER INFORMATION: Xaa at position 10 is Tyr-NH2

<400> SEQUENCE: 49

Asn Ile Pro Xaa Leu Tyr Xaa Phe Ala Xaa
1               5                   10
```

<210> SEQ ID NO 50
<211> LENGTH: 10
<212> TYPE: PRT
<213> ORGANISM: Artificial Sequence
<220> FEATURE:
<223> OTHER INFORMATION: Chemically synthesized

<400> SEQUENCE: 50

Asn Ile Pro Gly Leu Tyr Tyr Phe Ala Tyr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (10)..(10)
<223> OTHER INFORMATION: Xaa at position 10 is D-Ser

<400> SEQUENCE: 51

Xaa Ile Pro Gly Leu Tyr Tyr Phe Ala Xaa
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva

<400> SEQUENCE: 52

Asn Ile Pro Xaa Leu Tyr Tyr Phe Ala Tyr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa at position 7 is D-Ser

<400> SEQUENCE: 53

Asn Ile Pro Gly Leu Tyr Xaa Phe Ala Tyr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)

```
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser

<400> SEQUENCE: 54

Asn Ile Pro Xaa Leu Tyr Xaa Phe Ala Tyr
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (11)..(11)
<223> OTHER INFORMATION: Xaa at position 11 is bAla

<400> SEQUENCE: 55

Asn Ile Pro Gly Leu Tyr Tyr Phe Ala Tyr Xaa
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: Xaa at position 1 is D-Asn
<220> FEATURE:
<221> NAME/KEY: MISC_FEATURE
<222> LOCATION: (10)..(10)
<223> OTHER INFORMATION: Xaa at position 10 is D-Ser
<220> FEATURE:
<221> NAME/KEY: MISC_FEATURE
<222> LOCATION: (11)..(11)
<223> OTHER INFORMATION: Xaa at position 11 is bAla

<400> SEQUENCE: 56

Xaa Ile Pro Gly Leu Tyr Tyr Phe Ala Xaa Xaa
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (11)..(11)
<223> OTHER INFORMATION: Xaa at position 11 is bAla

<400> SEQUENCE: 57

Ala Ile Pro Xaa Leu Tyr Tyr Phe Ala Tyr Xaa
1               5                   10

<210> SEQ ID NO 58
<211> LENGTH: 11
<212> TYPE: PRT
<213> ORGANISM: Artificial Sequence
```

```
<220> FEATURE:
<223> OTHER INFORMATION: Chemically synthesized
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (11)..(11)
<223> OTHER INFORMATION: Xaa at position 11 is bAla

<400> SEQUENCE: 58

Asn Ile Pro Gly Leu Tyr Xaa Phe Ala Tyr Xaa
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (4)..(4)
<223> OTHER INFORMATION: Xaa at position 4 is Nva
<220> FEATURE:
<221> NAME/KEY: MISC_FEATURE
<222> LOCATION: (7)..(7)
<223> OTHER INFORMATION: Xaa at position 7 is D-Ser
<220> FEATURE:
<221> NAME/KEY: MISC_FEATURE
<222> LOCATION: (11)..(11)
<223> OTHER INFORMATION: Xaa at position 11 is bAla

<400> SEQUENCE: 59

Asn Ile Pro Xaa Leu Tyr Xaa Phe Ala Tyr Xaa
1               5                   10

<210> SEQ ID NO 60
<211> LENGTH: 15
<212> TYPE: PRT
<213> ORGANISM: Homo sapiens

<400> SEQUENCE: 60

Arg Pro Asn Met Tyr Phe Met Ala Pro Leu Gln Glu Lys Val Val
1               5                   10                  15

<210> SEQ ID NO 61
<211> LENGTH: 10
<212> TYPE: PRT
<213> ORGANISM: Artificial Sequence
<220> FEATURE:
<223> OTHER INFORMATION: Chemically synthesized

<400> SEQUENCE: 61

Asn Ile Pro Gly Leu Tyr Tyr Phe Ala Tyr
1               5                   10

<210> SEQ ID NO 62
<211> LENGTH: 8
<212> TYPE: PRT
<213> ORGANISM: Homo sapiens

<400> SEQUENCE: 62

Ile Pro Gly Leu Tyr Tyr Phe Ala
1               5
```